US007179473B2

(12) United States Patent
Meyers

(10) Patent No.: US 7,179,473 B2
(45) Date of Patent: *Feb. 20, 2007

(54) ATTENUATED PESTIVIRUSES

(75) Inventor: Gregor Meyers, Walddorfhaeslach (DE)

(73) Assignee: Boehringer Ingelheim Vetmedica GmbH, Ingelheim am Rhein (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 670 days.

(21) Appl. No.: 09/325,542

(22) Filed: Jun. 4, 1999

(65) Prior Publication Data

US 2003/0044426 A1 Mar. 6, 2003

Related U.S. Application Data

(60) Provisional application No. 60/092,027, filed on Jul. 7, 1998.

(30) Foreign Application Priority Data

Jun. 5, 1998 (EP) ............................. 98110356

(51) Int. Cl.
 *A61K 39/12* (2006.01)

(52) U.S. Cl. ............................... 424/218.1; 424/184.1; 424/204.1; 424/205.1; 424/434; 435/440; 435/442

(58) Field of Classification Search ................. 424/434, 424/184.1, 204.1, 205.1, 218.1, 220.1; 435/440, 435/442
 See application file for complete search history.

(56) References Cited

U.S. PATENT DOCUMENTS

| 4,719,177 | A | 1/1988 | Baltimore et al. |
| 5,206,163 | A | 4/1993 | Renard et al. |
| 6,001,613 | A | 12/1999 | Donis et al. |
| 6,168,942 | B1 | 1/2001 | Cao et al. |
| 6,610,305 | B1 | 8/2003 | Elbers et al. |
| 2004/0038198 | A1 | 2/2004 | Elbers et al. |

FOREIGN PATENT DOCUMENTS

EP 0 794 257 A1 9/1997

OTHER PUBLICATIONS

Stedman's Medical Dictionary. 27th Edition, Internet Edition. HTTP://www.pdrel.com/pdr/static.htm?path=pdrel/stedmans/v/s43000.htm.*
Baker, J.C., "Bovine viral diarrhea virus: A review," *J. Am. Vet. Med. Assoc.* 190:1449–1458 (Jun. 1987).
Becher, P., et al., "Further Characterization of Border Disease Virus Isolates: Evidence for the Presence of More Than Three Species Within the Genus Pestivirus," *Virol.* 209:200–206 (May 1995).
Donis, R.O. et al., "Neutralizing Monoclonal Antibodies to Bovine Viral Diarrhoea Virus Bind to the 56K to 58K Glycoprotein," *J. Gen. Virol.* 69:77–86 (Jan. 1988).
Hulst, M.M. et al., "Glycoprotein E2 of Classical Swine Fever Virus: Expression in Insect Cells and Identification as a Ribnuclease," *Virol.* 200:558–565 (Jul. 1994).
Hulst, M.M. et al., "Inactivation of the RNase Activity of Glycoprotein $E^{rns}$ of Classical Swine Fever Virus Results in a Cytopathogenic Virus," *J. Virol.* 72:151–157 (Jan. 1998).
Kit, M. and Kit, S., "Sensitive glycoprotein gIII blocking ELISA to distinguish between pseudorabies (Aujeszky's disease) –infected and vaccinated pigs," *Vet. Microbiol.* 28:141–155 (Jul. 1991).
Meyers, G. et al., "Molecular Cloning and Nucleotide Sequence of the Genome of Hog Cholera Virus," *Virol.* 171:555–567 (Aug. 1989).
Meyers, G. et al., "Classical swine fever virus: recovery of infectious viruses from cDNA constructs and generation of recombinant cytopathogenic defective interfering particles," *J. Vrirol.* 70:1588–1595 (Mar. 1996).
Meyers, G. et al., "Recovery of Cytopathogenic and Non-cytopathogenic Bovine Viral Diarrhea Viruses from cDNA Constructs," *J. Virol.* 70:8606–8613 (Dec. 1996).
Moennig, V. and Plagemann, P.G.W., "The Pestiviruses," *Adv. Virus Res.* 41:53–98 (1992).
Paton, D.J. et al., "Epitope Mapping of the gp53 Envelope Protein of Bovine Viral Diarrhea Virus," *Virol.* 190:763–772 (Oct. 1992).
Pellerin, C. et al., "Identification of a New Group of Bovine Viral Diarrhea Virus Strains Associated with Severe Outbreaks and High Mortalities," *Virol.* 203:260–268 (Sep. 1994).
Rice, C.M., "*Flaviviridae*: The Viruses and Their Replication,"*Fields Virology* (3rd ed.), Fields, B.N., Knipe, D.M., & Howley, P.M., eds., Lippincott–Raven Publishers, Philadelphia, PA, pp. 931–959 (1996).
Rümenapf, T. et al., "Processing of the Envelope Glycoproteins of Pestiviruses," *J. Virol.* 67:3288–3294 (Jun. 1993).
Schneider, R. et al., "Identification of a Structural Glycoprotein of an RNA Virus as a Ribonuclease," *Science* 261:1169–1171 (Aug. 1993).
Stark, R. et al., "Processing of Pestivirus Polyprotein: Cleavage Site between Autoprotease and Nucleocapsid Protein of Classical Swine Fever Virus," *J. Virol.* 67:7088–7095 (Dec. 1993).

(Continued)

*Primary Examiner*—Lynette R. F. Smith
*Assistant Examiner*—Robert A. Zeman
(74) *Attorney, Agent, or Firm*—Sterne, Kessler, Goldstein & Fox P.L.L.C.

(57) ABSTRACT

This invention relates to attenuated pestiviruses characterised in that their enzymatic activity residing in glycoprotein $E^{RNS}$ is inactivated, methods of preparing, using and detecting these.

49 Claims, 7 Drawing Sheets

OTHER PUBLICATIONS

Thiel, H.–J. et al., "Hog Cholera Virus: Molecular Composition of Virions from a Pestivirus," *J. Virol.* 65:4705–4712 (Sep. 1991).

Thiel, H.–J., et al., "Pestiviruses" in *Fields Virology*, (3rd ed.) Fields, B.N., Knipe, D.M., & Howley, P.M.,eds., Lippincott–Raven Publishers, Philadelphia, PA, pp. 1059–1073 (1996).

van Rijn, P.A. et al., "Epitope mapping of envelope glycoprotein E1 of hog cholera virus strain Brescia," *J. Gen. Virol.* 74:2053–2060 (Oct. 1993).

Weiland, E. et al., "Development of monoclonal neutralizing antibodies against bovine viral diarrhea virus after pretreatment of mice with normal bovine cells and cyclophosphamide," *J. Virol. Methods* 24:237–244 (Apr./May 1989).

Weiland, E. et al., "Pestivirus Glycoprotein Which Induces Neutralizing Antibodies Forms Part of a Disulfide–Linked Heterodimer," *J. Virol.* 64:3563–3569 (Aug. 1990).

Weiland, E. et al., "A Second Envelope Glycoprotein Mediates Neutralization of a Pestivirus, Hog Cholera Virus," *J. Virol.* 66:3677–3682 (Jun. 1992).

Windisch, J.M. et al., "RNase of Classical Swine Fever Virus: Biochemical Characterization and Inhibition by Virus–Neutralizing Monoclonal Antibodies," *J. Virol.* 70:352–358 (Jan. 1996).

Behrens, S–E., et al., "Characterization of an Autonomous Subgenomic Pestivirus RNA Replicon," *J. Virol.* 72:2364–2372, American Society for Microbiology (1998).

Boyer, J–C., and Haenni, A–L., "Minireview: Infectious Transcripts and cDNA Clones of RNA Viruses," *Virol.* 198:415–428, Elsevier Science B.V. (1994).

Brock, K.V., et al., "Nucleotide sequencing of 5' and 3' termini of bovine viral diarrhea virus by RNA ligation and PCR," *J. Virol. Methods* 38:39–46, North–Holland Biomedical Press (1992).

Chambers, T.J., et al., "Mutagenesis of the yellow fever virus NS2B protein: effects on proteolytic processing, NS2B–NS3 complex formation, and viral replication," *J. Virol.* 67:6797–6807, American Society for Microbiology (1993).

Chon, S.K., et al., "Genetic analysis of the internal ribosome entry segment of bovine viral diarrhea virus," *Virology* 251:370–382, Elsevier Science B.V. (1998).

Collett, M.S., et al., "Molecular cloning and nucleotide sequence of the pestivirus bovine viral diarrhea virus," *Virology* 165:191–199, Elsevier Science B.V. (1988).

Cortese, V.S., et al., "Clinical And Immunologic Responses Of Vaccinated And Unvaccinated Calves To Infection With A Virulent Type–II Isolate Of Bovine Viral Diarrhea Virus," *J. Am. Vet. Med. Assoc.* 213:1312–1319, American Veterinary Medical Association (1998).

Cortese, V.S., et al., "Specificity And Duration Of Neutralizing Antibodies Induced In Healthy Cattle After Administration Of A Modified–Live Virus Vaccine Against Bovine Viral Diarrhea," *Am. J. Vet. Res.* 59:848–850, American Veterinary Medical Association (1998).

Fekadu, M., et al., "Immunogenicity, Efficacy And Safety Of An Oral Rabies Vaccine (SAG–2) In Dogs," *Vaccine* 14:465–468, Elsevier Science B.V. (1996).

Gu, B., et al., "The RNA Helicase and Nucleotide Triphosphatase Activities of the Bovine Viral Diarrhea Virus NS3 Protein Are Essential for Viral Replication," *J. Virol.* 74:1794–1800, American Society for Microbiology (2000).

Houe, H., et al., "Application Of Antibody Titers Against Bovine Viral Diarrhea Virus (BVDV) As a Measure To Detect Herds With Cattle Persistently Infected With BVDV," *J. Vet. Diagn. Invest.* 7:327–332, American Association Of Veterinary Laboratory Diagnosticians (1995).

Huang, Q.S., et al., "An in vitro ligation and transfection system for inserting DNA sequences into the latency–associated transcripts (LATs) gene of herpes simplex virus type 1," *Gene Ther.* 1:300–306, Nature Publishing Group (1994).

Kümmerer, B.M., and Meyers, G., "Correlation between Point Mutations in NS2 and the Viability and Cytopathogenicity of Bovine Viral Diarrhea Virus Strain Oregon Analyzed with an Infectious cDNA Clone," *J. Virol.* 74:390–400, American Society for Microbiology (2000).

Kupfermann, H., et al., "Bovine viral diarrhea virus: characterization of a cytopathogenic defective interfering particle with two internal deletions," *J. Virol.* 70:8175–8181, American Society for Microbiology (1996).

Lai, C.J., et al., "Infectious RNA transcribed from stably cloned full–length cDNA of dengue type 4 virus," *Proc. Natl. Acad. Sci.* 88:5139–5143, National Academy of Sciences (1991).

Men, R., et al., "Dengue type 4 virus mutants containing deletions in the 3' noncoding region of the RNA genome: analysis of growth restriction in cell culture and altered viremia pattern and immunogenicity in rhesus monkeys," *J. Virol.* 70:3930–3937, American Society for Microbiology (1996).

Mendez, E., et al., "Infectious Bovine Viral Diarrhea Virus (Strain NADL) RNA from Stable cDNA Clones: a Cellular Insert Determines NS3 Production and Viral Cytopathogenicity," *J. Virol.* 72:4737–4745, American Society for Microbiology (1998).

Meyers, G., and Thiel, H–J., "Molecular Characterization of Pestiviruses," *Adv. Virus Res.* 47:53–118, Academic Press (1996).

Moormann, R.J., et al., "Infectious RNA transcribed from an engineered full–length cDNA template of the genome of a pestivirus," *J. Virol.* 70:763–770, American Society for Microbiology (1996).

Moser, C., et al., "A Recombinant Classical Swine Fever Virus Stably Expresses a Marker Gene," *J. Virol.* 72:5318–5322, American Society for Microbiology (1998).

Murphy, F.A., et al., *Veterinary Virology*, Academic Press, San Diego, CA, pp. 564–566 (1999).

Paoletti, E., et al., "Highly attenuated poxvirus vectors: NYVAC, ALVAC and TROVAC," *Dev. Biol. Stand.* 84:159–163, Basel Karger (1995).

Ramig, R.F., "Principles of Animal Virus Genetics," in *Fundamental Virology*, Knipe, D.M., et al., eds., Lippincott Williams & Wilkins, Philadelphia, PA, p. 96 (1991).

Rice, C.M., et al., "Transcription of infectious yellow fever RNA from full–length cDNA templates produced by *in vitro* ligation," *New Biol.* 1:285–296, W.B. Saunders (1989).

Ruggli, N., et al., "Nucleotide sequence of classical swine fever virus strain Alfort/187 and transcription of infectious RNA from stably cloned full–length cDNA," *J. Virol.* 70:3478–3487, American Society for Microbiology (1996).

Rümenapf, T., et al., "N–Terminal Protease of Pestiviruses: Identification of Putative Catalytic Residues by Site–Directed Mutagenesis," *J. Virol.* 72:2544–2547, American Society for Microbiology (1998).

Sumiyoshi, H., et al., "Infectious Japanese encephalitis virus RNA can be synthesized from in vitro–ligated cDNA templates," *J. Virol.* 66:5425–5431, American Society for Microbiology (1992).

Tratschin, J–D., et al., "Classical Swine Fever Virus Leader Proteinase $N^{pro}$ Is Not Required for Viral Replication in Cell Culture," *J. Virol.* 72:7681–7684, American Society for Microbiology (1998).

van Oirschot, J.T., et al., "Vaccination of cattle against bovine viral diarrhea," *Vet. Microbiol.* 64:169–183, Elsevier Science B.V. (1999).

Vassilev, V.B., "Authentic and chimeric full–length genomic cDNA clones of bovine viral diarrhea virus that yield infectious transcripts," *J. Virol.* 71:471–478, American Society for Microbiology (1997).

Windisch, J.M., et al., "RNase of Classical Swine Fever Virus: Biochemical Characterization and Inhibition by Virus–Neutralizing Monoclonal Antibodies," *J. Virol.* 70:352–358, American Society for Microbiology (1996).

Yu, Z., et al., "Genetic engineering of a *Lymantria dispar* nuclear polyhedrosis virus for expression of foreign genes," *J. Gen. Virol.* 73:1509–1514, Society For General Microbiology (1992).

European Search Report for European Patent Application No. EP 02 00 3408, mailed Dec. 15, 2003, The Hague, Netherlands.

* cited by examiner

1   Met Glu Leu Asn His Phe Glu Leu Leu Tyr Lys Thr Ser Lys Gln Lys Pro Val Gly  19
20  Val Glu Glu Pro Val Tyr Asp Thr Ala Gly Arg Pro Leu Phe Gly Asn Pro Ser Glu Val
40  His Pro Gln Ser Thr Leu Lys Leu Pro His Asp Arg Gly Arg Gly Asp Ile Arg Thr Thr
60  Leu Arg Asp Leu Pro Arg Lys Gly Asp Cys Arg Ser Gly Asn His Leu Gly Pro Val Ser
80  Gly Ile Tyr Ile Lys Pro Gly Pro Val Tyr Tyr Gln Asp Tyr Thr Gly Pro Val Tyr His
100 Arg Ala Pro Leu Glu Phe Phe Asp Glu Ala Gln Phe Cys Glu Val Thr Lys Arg Ile Gly
120 Arg Val Thr Gly Ser Asp Gly Lys Leu Tyr His Ile Tyr Val Cys Val Asp Gly Cys Ile
140 Leu Leu Lys Leu Ala Lys Arg Gly Thr Pro Arg Thr Leu Lys Trp Ile Arg Asn Phe Thr
160 Asn Cys Pro Leu Trp Val Thr Ser Cys Ser Asp Asp Gly Ala Ser Gly Ser Lys Asp Lys
180 Lys Pro Asp Arg Met Asn Lys Gly Lys Leu Lys Ile Ala Pro Arg Glu His Glu Lys Asp
200 Ser Lys Thr Lys Pro Pro Asp Ala Thr Ile Val Val Glu Gly Val Lys Tyr Gln Ile Lys
220 Lys Lys Gly Lys Val Lys Gly Lys Asn Thr Gln Asp Gly Leu Tyr His Asn Lys Asn Lys
240 Pro Pro Glu Ser Arg Lys Lys Leu Glu Lys Ala Leu Leu Ala Trp Ala Val Ile Thr Ile
260 Leu Leu Tyr Gln Pro Val Ala Ala Glu Asn Ile Thr Gln Trp Asn Leu Ser Asp Asn Gly
280 Thr Asn Gly Ile Gln Arg Ala Met Tyr Leu Arg Gly Val Asn Arg <u>Ser Leu His Gly Ile</u>
300 <u>Trp Pro Glu Lys Ile Cys Lys Gly</u> Val Pro Thr His Leu Ala Thr Asp Thr Glu Leu Lys
320 Glu Ile Arg Gly Met Met Asp Ala Ser Glu Arg Thr Asn Tyr Thr Cys Cys Arg <u>Leu Gln</u>
340 <u>Arg His Glu Trp Asn Lys His Gly Trp Cys Asn Trp Tyr Asn Ile Asp Pro Trp</u> Ile Gln
360 Leu Met Asn Arg Thr Gln Thr Asn Leu Thr Glu Gly Pro Pro Asp Lys Glu Cys Ala Val
380 Thr Cys Arg Tyr Asp Lys Asn Thr Asp Val Asn Val Val Thr Gln Ala Arg Asn Arg Pro
400 Thr Thr Leu Thr Gly Cys Lys Lys Gly Lys Asn Phe Ser Phe Ala Gly Thr Val Ile Glu
420 Gly Pro Cys Asn Phe Asn Val Ser Val Glu Asp Ile Leu Tyr Gly Asp His Glu Cys Gly
440 Ser Leu Leu Gln Asp Thr Ala Leu Tyr Leu Leu Asp Gly Met Thr Asn Thr Ile Glu Asn
460 Ala Arg Gln Gly Ala Ala Arg Val Thr Ser Trp Leu Gly Arg Gln Leu Ser Thr Ala Gly
480 Lys Lys Leu Glu Arg Arg Ser Lys Thr Trp Phe Gly Ala Tyr Ala Leu  495

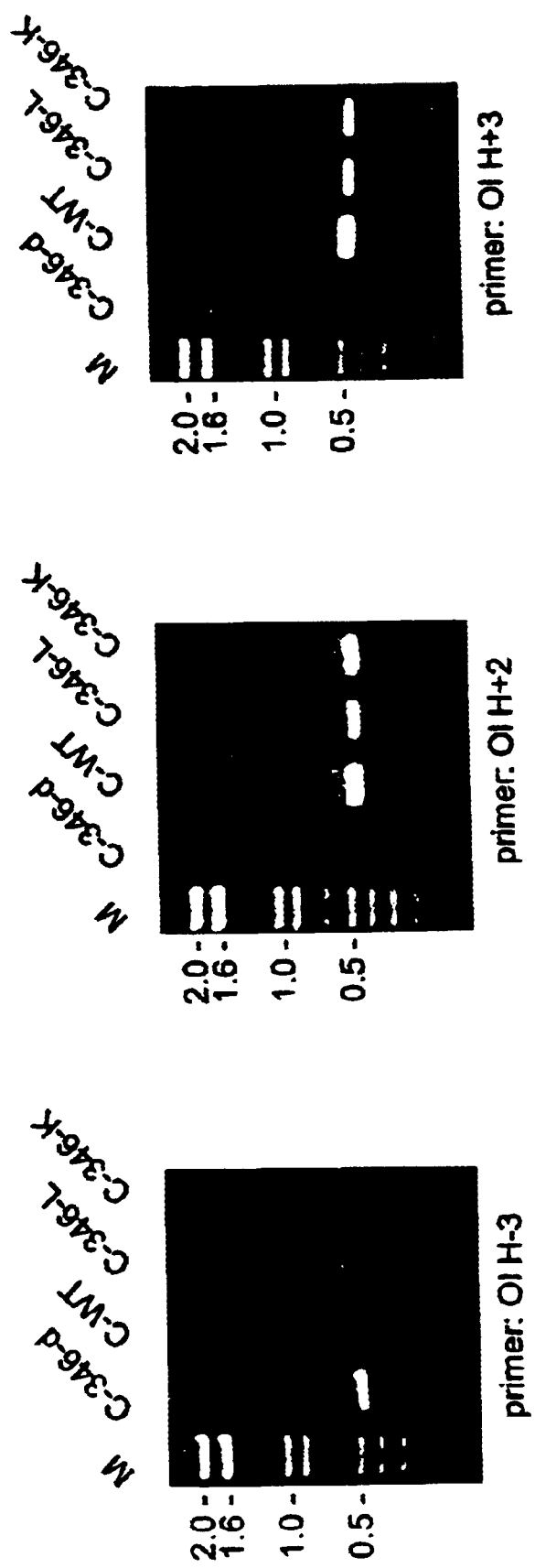

SEQUENCE LISTING

<160> NUMBER OF SEQ ID NOS: 34

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 1
aggagcttac ttgggatctg                                              20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 2
ggaacaaact tggatggtgt                                              20

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 3
acaggagctt aaaagggatc tggc                                         24

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 4
atggaacaaa aagggatggt gtaa                                         24

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 5
gaatggaaca aaggatggtg taac                                         24

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 6
catgaatgga acaaaggttg gtgcaactgg                                   30

<210> SEQ ID NO 7
<211> LENGTH: 11

-continued

```
<212> TYPE: PRT
<213> ORGANISM: Artificial Sequence
<220> FEATURE:
<223> OTHER INFORMATION: Description of Artificial Sequence:
      Introduced Sequence in
      RNase motif

<400> SEQUENCE: 7

Ser Leu His Gly Ile Trp Pro Glu Lys Ile Cys
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence:
      Introduced Sequence in
      RNase motif

<400> SEQUENCE: 8

Arg His Glu Trp Asn Lys His Gly Trp Cys Asn Trp
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence:
      Introduced Sequence in
      RNase motif

<400> SEQUENCE: 9

Ser Leu Leu Gly Ile Trp Pro Glu Lys Ile Cys
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence:
      Introduced Sequence in
      RNase motif

<400> SEQUENCE: 10

Arg His Glu Trp Asn Lys Leu Gly Trp Cys Asn Trp
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence:
      Introduced Sequence in
      RNase motif

<400> SEQUENCE: 11

Ser Leu Lys Gly Ile Trp Pro Glu Lys Ile Cys
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence:
```

-continued

Introduced Sequence in
     RNase motif

<400> SEQUENCE: 12

Arg His Glu Trp Asn Lys Lys Gly Trp Cys Asn Trp
 1               5                 10

<210> SEQ ID NO 13
<211> LENGTH: 11
<212> TYPE: PRT
<213> ORGANISM: Artificial Sequence
<220> FEATURE:
<221> NAME/KEY: UNSURE
<222> LOCATION: (3)
<223> OTHER INFORMATION: Description of Artificial Sequence:
     Introduced Sequence in
     RNase motif

<400> SEQUENCE: 13

Ser Leu Xaa Gly Ile Trp Pro Glu Lys Ile Cys
 1               5                 10

<210> SEQ ID NO 14
<211> LENGTH: 12
<212> TYPE: PRT
<213> ORGANISM: Artificial Sequence
<220> FEATURE:
<221> NAME/KEY: UNSURE
<222> LOCATION: (7)
<223> OTHER INFORMATION: Description of Artificial Sequence:
     Introduced Sequence in
     RNase motif

<400> SEQUENCE: 14

Arg His Glu Trp Asn Lys Xaa Gly Trp Cys Asn Trp
 1               5                 10

<210> SEQ ID NO 15
<211> LENGTH: 11
<212> TYPE: PRT
<213> ORGANISM: Artificial Sequence
<220> FEATURE:
<221> NAME/KEY: UNSURE
<222> LOCATION: (2)..(4)
<223> OTHER INFORMATION: Description of Artificial Sequence:
     Introduced Sequence in
     RNase motif

<400> SEQUENCE: 15

Ser Xaa Xaa Xaa Ile Trp Pro Glu Lys Ile Cys
 1               5                 10

<210> SEQ ID NO 16
<211> LENGTH: 12
<212> TYPE: PRT
<213> ORGANISM: Artificial Sequence
<220> FEATURE:
<221> NAME/KEY: UNSURE
<222> LOCATION: (6)..(8)
<223> OTHER INFORMATION: Description of Artificial Sequence:
     Introduced Sequence in
     RNase motif

<400> SEQUENCE: 16

Arg His Glu Trp Asn Xaa Xaa Xaa Trp Cys Asn Trp
 1               5                 10

<210> SEQ ID NO 17
<211> LENGTH: 12

```
<212> TYPE: PRT
<213> ORGANISM: Artificial Sequence
<220> FEATURE:
<221> NAME/KEY: UNSURE
<222> LOCATION: (6)..(7)
<223> OTHER INFORMATION: Description of Artificial Sequence:
      Introduced Sequence in
      RNase motif

<400> SEQUENCE: 17

Arg His Glu Trp Asn Xaa Xaa Gly Trp Cys Asn Trp
 1               5                  10

<210> SEQ ID NO 18
<211> LENGTH: 12
<212> TYPE: PRT
<213> ORGANISM: Artificial Sequence
<220> FEATURE:
<221> NAME/KEY: UNSURE
<222> LOCATION: (7)..(8)
<223> OTHER INFORMATION: Description of Artificial Sequence:
      Introduced Sequence in
      RNase motif

<400> SEQUENCE: 18

Arg His Glu Trp Asn Lys Xaa Xaa Trp Cys Asn Trp
 1               5                  10

<210> SEQ ID NO 19
<211> LENGTH: 12
<212> TYPE: PRT
<213> ORGANISM: Artificial Sequence
<220> FEATURE:
<221> NAME/KEY: UNSURE
<222> LOCATION: (3)
<223> OTHER INFORMATION: Description of Artificial Sequence:
      Introduced Sequence in
      RNase motif

<400> SEQUENCE: 19

Arg His Xaa Trp Asn Lys His Gly Trp Cys Asn Trp
 1               5                  10

<210> SEQ ID NO 20
<211> LENGTH: 12
<212> TYPE: PRT
<213> ORGANISM: Artificial Sequence
<220> FEATURE:
<221> NAME/KEY: UNSURE
<222> LOCATION: (3)
<221> NAME/KEY: UNSURE
<222> LOCATION: (7)
<223> OTHER INFORMATION: Description of Artificial Sequence:
      Introduced Sequence in
      RNase motif

<400> SEQUENCE: 20

Arg His Xaa Trp Asn Lys Xaa Gly Trp Cys Asn Trp
 1               5                  10

<210> SEQ ID NO 21
<211> LENGTH: 11
<212> TYPE: PRT
<213> ORGANISM: Artificial Sequence
<220> FEATURE:
<221> NAME/KEY: UNSURE
<222> LOCATION: (7)
<223> OTHER INFORMATION: Description of Artificial Sequence:
      Introduced Sequence in
      RNase motif
```

```
<400> SEQUENCE: 21

Ser Leu His Gly Ile Trp Xaa Glu Lys Ile Cys
 1               5                  10

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence:
      Introduced Sequence in
      RNase motif

<400> SEQUENCE: 22

Gly Leu His Gly Ile Trp Pro Glu Lys Ile Cys
 1               5                  10

<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence:
      Introduced Sequence in
      RNase motif

<400> SEQUENCE: 23

Ser Leu His Gly Ile Gly Pro Glu Lys Ile Cys
 1               5                  10

<210> SEQ ID NO 24
<211> LENGTH: 11
<212> TYPE: PRT
<213> ORGANISM: Artificial Sequence
<220> FEATURE:
<223> OTHER INFORMATION: Description of Artificial Sequence:
      Introduced Sequence in
      RNase motif

<400> SEQUENCE: 24

Ser Leu His Gly Ile Trp Pro Ala Lys Ile Cys
 1               5                  10

<210> SEQ ID NO 25
<211> LENGTH: 11
<212> TYPE: PRT
<213> ORGANISM: Artificial Sequence
<220> FEATURE:
<223> OTHER INFORMATION: Description of Artificial Sequence:
      Introduced Sequence in
      RNase motif

<400> SEQUENCE: 25

Ser Leu His Gly Ile Trp Pro Glu Lys Ile Gly
 1               5                  10

<210> SEQ ID NO 26
<211> LENGTH: 11
<212> TYPE: PRT
<213> ORGANISM: Artificial Sequence
<220> FEATURE:
<223> OTHER INFORMATION: Description of Artificial Sequence:
      Introduced Sequence in
      RNase motif

<400> SEQUENCE: 26

Ser Leu His Gly Ile Gly Pro Ala Lys Ile Cys
 1               5                  10
```

```
<210> SEQ ID NO 27
<211> LENGTH: 12
<212> TYPE: PRT
<213> ORGANISM: Artificial Sequence
<220> FEATURE:
<223> OTHER INFORMATION: Description of Artificial Sequence:
      Introduced Sequence in
      RNase motif

<400> SEQUENCE: 27

Gly His Glu Trp Asn Lys His Gly Trp Cys Asn Trp
 1               5                  10

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence:
      Introduced Sequence in
      RNase motif

<400> SEQUENCE: 28

Arg His Glu Gly Asn Lys His Gly Trp Cys Asn Trp
 1               5                  10

<210> SEQ ID NO 29
<211> LENGTH: 12
<212> TYPE: PRT
<213> ORGANISM: Artificial Sequence
<220> FEATURE:
<223> OTHER INFORMATION: Description of Artificial Sequence:
      Introduced Sequence in
      RNase motif

<400> SEQUENCE: 29

Arg His Glu Trp Asn Ala His Gly Trp Cys Asn Trp
 1               5                  10

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 30
tggaacaaag gatggtgt                                                 18

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence:
      Primer

<400> SEQUENCE: 31
tggaacaaac atggatgg                                                 18

<210> SEQ ID NO 32
<211> LENGTH: 18
<212> TYPE: DNA
<213> ORGANISM: Artificial Sequence
<220> FEATURE:
<223> OTHER INFORMATION: Description of Artificial Sequence:
      Primer
```

-continued

<400> SEQUENCE: 32
gaatggaaca aacatgga                                                      18

<210> SEQ ID NO 33
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 33
ggaattctca ggcataggca ccaaaccagg                                         30

<210> SEQ ID NO 34
<211> LENGTH: 495
<212> TYPE: PRT
<213> ORGANISM: Classical swine fever virus (CSFV)

<400> SEQUENCE: 34

```
Met Glu Leu Asn His Phe Glu Leu Leu Tyr Lys Thr Ser Lys Gln Lys
  1               5                  10                  15

Pro Val Gly Val Glu Pro Val Tyr Asp Thr Ala Gly Arg Pro Leu
                 20                  25                  30

Phe Gly Asn Pro Ser Glu Val His Pro Gln Ser Thr Leu Lys Leu Pro
             35                  40                  45

His Asp Arg Gly Arg Gly Asp Ile Arg Thr Thr Leu Arg Asp Leu Pro
         50                  55                  60

Arg Lys Gly Asp Cys Arg Ser Gly Asn His Leu Gly Pro Val Ser Gly
 65                  70                  75                  80

Ile Tyr Ile Lys Pro Gly Pro Val Tyr Tyr Gln Asp Tyr Thr Gly Pro
                 85                  90                  95

Val Tyr His Arg Ala Pro Leu Glu Phe Phe Asp Glu Ala Gln Phe Cys
            100                 105                 110

Glu Val Thr Lys Arg Ile Gly Arg Val Thr Gly Ser Asp Gly Lys Leu
        115                 120                 125

Tyr His Ile Tyr Val Cys Val Asp Gly Cys Ile Leu Leu Lys Leu Ala
    130                 135                 140

Lys Arg Gly Thr Pro Arg Thr Leu Lys Trp Ile Arg Asn Phe Thr Asn
145                 150                 155                 160

Cys Pro Leu Trp Val Thr Ser Cys Ser Asp Asp Gly Ala Ser Gly Ser
                165                 170                 175

Lys Asp Lys Lys Pro Asp Arg Met Asn Lys Gly Lys Leu Lys Ile Ala
            180                 185                 190

Pro Arg Glu His Glu Lys Asp Ser Lys Thr Lys Pro Pro Asp Ala Thr
        195                 200                 205

Ile Val Val Glu Gly Val Lys Tyr Gln Ile Lys Lys Gly Lys Val
    210                 215                 220

Lys Gly Lys Asn Thr Gln Asp Gly Leu Tyr His Asn Lys Asn Lys Pro
225                 230                 235                 240

Pro Glu Ser Arg Lys Lys Leu Glu Lys Ala Leu Leu Ala Trp Ala Val
                245                 250                 255

Ile Thr Ile Leu Leu Tyr Gln Pro Val Ala Ala Glu Asn Ile Thr Gln
            260                 265                 270

Trp Asn Leu Ser Asp Asn Gly Thr Asn Gly Ile Gln Arg Ala Met Tyr
        275                 280                 285
```

```
Leu Arg Gly Val Asn Arg Ser Leu His Gly Ile Trp Pro Glu Lys Ile
    290             295             300
Cys Lys Gly Val Pro Thr His Leu Ala Thr Asp Thr Glu Leu Lys Glu
305             310             315             320
Ile Arg Gly Met Met Asp Ala Ser Glu Arg Thr Asn Tyr Thr Cys Cys
                325             330             335
Arg Leu Gln Arg His Glu Trp Asn Lys His Gly Trp Cys Asn Trp Tyr
            340             345             350
Asn Ile Asp Pro Trp Ile Gln Leu Met Asn Arg Thr Gln Thr Asn Leu
        355             360             365
Thr Glu Gly Pro Pro Asp Lys Glu Cys Ala Val Thr Cys Arg Tyr Asp
    370             375             380
Lys Asn Thr Asp Val Asn Val Val Thr Gln Ala Arg Asn Arg Pro Thr
385             390             395             400
Thr Leu Thr Gly Cys Lys Lys Gly Lys Asn Phe Ser Phe Ala Gly Thr
                405             410             415
Val Ile Glu Gly Pro Cys Asn Phe Asn Val Ser Val Glu Asp Ile Leu
                420             425             430
Tyr Gly Asp His Glu Cys Gly Ser Leu Leu Gln Asp Thr Ala Leu Tyr
            435             440             445
Leu Leu Asp Gly Met Thr Asn Thr Ile Glu Asn Ala Arg Gln Gly Ala
    450             455             460
Ala Arg Val Thr Ser Trp Leu Gly Arg Gln Leu Ser Thr Ala Gly Lys
465             470             475             480
Lys Leu Glu Arg Arg Ser Lys Thr Trp Phe Gly Ala Tyr Ala Leu
                485             490             495
```

ATTENUATED PESTIVIRUSES

This application claims the benefit of provisional application 60/092,027 filed Jul. 7, 1998.

FIELD OF THE INVENTION

The present invention relates to a method for attenuating pestiviruses by inactivating the ribonuclease activity (RNase activity) residing in glycoprotein $E^{RNS}$. The invention also relates to pestiviruses attenuated according to the invention, nucleic acids for preparing such pestiviruses, vaccines and pharmaceutical compositions comprising the attenuated pestiviruses of the invention. The invention further relates to methods for distinguishing between the attenuated viruses of the invention and pathogenic viruses.

BACKGROUND OF THE INVENTION

Pestiviruses are causative agents of economically important diseases of animals in many countries worldwide. Presently known virus isolates have been grouped into three different species which together form one genus within the family Flaviviridae.

I Bovine viral diarrhea virus (BVDV) causes bovine viral diarrhea (BVD) and mucosal disease (MD) in cattle (Baker, 1987; Moennig and Plagemann, 1992; Thiel et al., 1996).

II Classical swine fever virus (CSFV), formerly named hog cholera virus, is responsible for classical swine fever (CSF) or hog cholera (HC) (Moennig and Plagemann, 1992; Thiel et al., 1996).

III Border disease virus (BDV) is typically found in sheep and causes border disease (BD). Symptoms similar to MD in cattle have also been described to occur after intrauterine infection of lambs with BDV (Moennig and Plagemann, 1992; Thiel et al., 1996).

An alternative classification of pestiviruses is provided by Becher et al. (1995) or others.

Pestiviruses are small enveloped viruses with a single stranded RNA genome of positive polarity lacking both 5' cap and 3' poly(A) sequences. The viral genome codes for a polyprotein of about 4000 amino acids giving rise to final cleavage products by co- and posttranslational processing involving cellular and viral proteases. The viral proteins are arranged in the polyprotein in the order $NH_2$-$N^{pro}$-C-$E^{RNS}$-E1-E2-p7-NS2-NS3-NS4A-NS4B-NS5A-NS5B-COOH (Rice, 1996). Protein C and the glycoproteins $E^{RNS}$, E1 and E2 represent structural components of the pestivirus virion (Thiel et al., 1991). E2 and to a lesser extent $E^{RNS}$ were found to be targets for antibody neutralization (Donis et al., 1988; Paton et al., 1992; van Rijn et al., 1993; Weiland et al., 1990, 1992). $E^{RNS}$ lacks a membrane anchor and is secreted in considerable amounts from the infected cells; this protein has been reported to exhibit RNase activity (Hulst et al., 1994; Schneider et al., 1993; Windisch et al., 1996). The function of this enzymatic activity for the viral life cycle is presently unknown. In the case of a CSFV vaccine strain experimental destruction of the RNase by site directed mutagenesis has been reported to result in a cytopathogenic virus that has growth characteristics in cell culture equivalent to wild type virus (Hulst et al., 1998). The enzymatic activity depends on the presence of two stretches of amino acids conserved between the pestivirus $E^{RNS}$ and different known RNases of plant and fungal origin. Both of these conserved sequences contain a histidine residue (Schneider et al., 1993). Exchange of each of these residues against lysine in the $E^{RNS}$ protein of a CSFV vaccine strain resulted in the destruction of RNase activity (Hulst et al., 1998). Introduction of these mutations into the genome of the CSFV vaccine strain did not influence viral viability or growth properties but led to a virus exhibiting a slightly cytopathogenic phenotype (Hulst et al., 1998).

Vaccines comprising attenuated or killed viruses or viral proteins expressed in heterologous expression systems have been generated for CSFV and BVDV and are presently used. The structural basis of the attenuation of these viruses used as life vaccines is not known. This leads to the risk of unpredictable revertants by backmutation or recombination subsequent to vaccination. On the other hand, the efficacy of inactivated vaccines or heterologously expressed viral proteins (subunit vaccines) in the induction of immunity is rather low.

In general, live vaccines with defined mutations as a basis for attenuation would allow to avoid the disadvantages of the present generation of vaccines. Potential targets for attenuating mutations in pestiviruses are not available at present.

A further advantage of said attenuating mutations lies in their molecular uniqueness which allows to use them as distinctive labels for an attenuated pestiviruses and to distinguish them from pestiviruses from the field.

Because of the importance of an effective and safe as well as detectable prophylaxis and treatment of pestiviral infections, there is a strong need for live and specifically attenuated vaccines with a high potential for induction of immunity as well as a defined basis of attenuation which can also be distinguished from pathogenic pestiviruses.

Therefore, the technical problem underlying the present invention is to provide specifically attenuated and detectably labeled pestiviruses for use as live attenuated vaccines with a high efficiency for the induction of immunity which, as a result of this method, can also be distinguished from pathogenic pestiviruses from the field.

DISCLOSURE OF THE INVENTION

The solution to the above technical problem is achieved by the description and the embodiments characterized in the claims.

It has surprisingly been found that pestiviruses can be specifically attenuated by the inactivation of the RNase activity residing in glycoprotein $E^{RNS}$.

The attenuated pestiviruses now provide live vaccines of high immunogenicity.

Therefore, in one aspect the present invention provides a live vaccine comprising a pestivirus, wherein the RNase activity residing in glycoprotein $E^{RNS}$ is inactivated.

The term "vaccine" as used herein refers to a pharmaceutical composition comprising at least one immunologically active component that induces an immunological response in an animal and possibly but not necessarily one or more additional components that enhance the immunological activity of said active component. A vaccine may additionally comprise further components typical to pharmaceutical compostions. The immunologically active component of a vaccine may comprise complete live organisms in either its original form or as attenuated organisms in a so called modified live vaccine (MLV) or organisms inactivated by appropriate methods in a so called killed vaccine (KV). In another form the immunologically active component of a vaccine may comprise appropriate elements of said organisms (subunit vaccines) whereby these elements are generated either by destroying the whole organism or the growth cultures of such organisms and subsequent purification steps yielding in the desired structure(s), or by synthetic processes induced by an appropriate manipulation of a suitable system like, but not restricted to bacteria, insects, mammalian or other species plus subsequent isolation and purification procedures or by induction of said synthetic processes in the animal needing a vaccine by direct incorporation of genetic material using suitable pharmaceutical compositions (polynucleotide vaccination). A vaccine may comprise one or simultaneously more than one of the elements described above.

Additional components to enhance the immune response are constituents commonly referred to as adjuvants, like e.g. aluminiumhydroxide, mineral or other oils or ancillary molecules added to the vaccine or generated by the body after the respective induction by such additional components, like but not restricted to interferons, interleukins or growth factors.

A "pharmaceutical composition" essentially consists of one or more ingredients capable of modifying physiological e.g. immunological functions of the organism it is administered to, or of organisms living in or on its surface like but not restricted to antibiotics or antiparasitics, as well as other constituents added to it in order to achieve certain other objectives like, but not limited to, processing traits, sterility, stability, feasibility to administer the composition via enteral or parenteral routes such as oral, intranasal, intravenous, intramuscular, subcutaneous, intradermal or other suitable route, tolerance after administration, controlled release properties.

A vaccine of the invention refers to a vaccine as defined above, wherein one immunologically active component is a pestivirus or of pestiviral origin.

The term "live vaccine" refers to a vaccine comprising a living, in particular, a living viral active component.

The term "pestivirus" as used herein refers to all pestiviruses, characterized by belonging to the same genus as BVDV, CSFV and BDV within the family Flaviviridae and by their expression of glycoprotein $E^{RNS}$. Of course, said term also refers to all pestiviruses as characterized by Becher et al. (1995) or others that express glycoprotein $E^{RNS}$. "RNase activity" as used herein refers to the ability of the glycoprotein $E^{RNS}$ to hydrolyze RNA.

It should be noted that the term glycoprotein E0 is often used synonymously to glycoprotein $E^{RNS}$ in publications.

The term "inactivation of the RNase activity residing in said glycoprotein" refers to the inability or reduced capability of a modified glycoprotein $E^{RNS}$ to hydrolyze RNA as compared to the unmodified wild type of said glycoprotein $E^{RNS}$.

Inactivation of the RNase activity residing in glycoprotein $E^{RNS}$ can be achieved by deletions and/or mutations of at least one amino acid of said glycoprotein as demonstrated herein and by Hulst et al. (1998). Therefore, in a preferred embodiment the present invention relates to live vaccines, wherein said RNase activity is inactivated by deletions and/or mutations of at least one amino acid of said glycoprotein.

It has been shown that the glycoprotein $E^{RNS}$ forms a disulfide-bonded homodimer of about 97 kD, wherein each monomer consists of 227 amino acids corresponding to the amino acids 268 to 494 of the CSFV polyprotein as described by Rümenapf et al. (1993). The first 495 amino acids as expressed by the Alfort strain of CSFV are shown in FIG. 1 (SEQ ID NO: 34) for reference purpose only. The genome sequence of the Alfort strain of CSFV is available in the GenBank/EMBL data library under accession number J04358; alternatively, the amino acid sequence for the BVDV strain CP7 can be accessed in the GenBank/EMBL data library (accession number U63479). Two regions of amino acids are highly conserved in glycoprotein $E^{RNS}$ s as well as in some plant and fungal RNase-active proteins (Schneider et al., 1993). These two regions are of particular importance to the RNase enzymatic activity. The first region consists of the region at the amino acids at position 295 to 307 and the second region consists of the amino acids at position 338 to 357 of said viral polyprotein as exemplified by FIG. 1 for the Alfort strain of CSFV (numbering according to the published deduced amino acid sequence of CSFV strain Alfort (Meyers et al., 1989). The amino acids of particular importance to the RNase activity as mentioned above are by no means limited to the exact position as defined for the Alfort strain of CSFV but are simply used in an exemplary manner to point out the preferred amino acids being at that position or corresponding to that position in other strains such as found in BVDV, BDV and pestiviruses in general since they are highly conserved. For pestiviruses other than the CSFV Alfort strain the numbering of the positions of the preferred amino acids is often different but an expert in the field of the molecular biology of pestiviruses will easily identify these preferred amino acids by their position relative to the highly conserved amino acids of said glycoprotein. In one particular non-limiting example, the position of CSFV Alfort 346 is identical to position 349 of BVDV strain cp7.

As a consequence, the present invention relates in a more preferred embodiment to a vaccine of the invention, wherein said inactivating deletions and/or mutations are located at the amino acids at position 295 to 307 and/or position 338 to 357, as described in FIG. 1 for the CSFV Alfort strain in an exemplary manner or corresponding thereto in other strains, of said glycoprotein.

In a very preferred embodiment the present invention discloses that the inactivation of said RNase activity by deletion or mutation of the amino acid at position 346 of said glycoprotein leads to particularly useful live vaccines. Therefore, the present invention relates to vaccines according to the invention, wherein said Rnase activity is inactivated by deletion or mutation of the amino acid at position 346, as described in FIG. 1 for the CSFV Alfort strain in an exemplary manner or corresponding thereto in other strains, of said glycoprotein.

The present invention demonstrates that pestiviruses are viable and code for an $E^{RNS}$ protein without RNase activity when the histidine residue at position 346 of the viral polyprotein (numbering according to the published sequence of CSFV Alfort/Tübingen (Meyers et al., 1989)), which represents one of the conserved putative active site residues of the $E^{RNS}$ RNase, is deleted. It has also been demonstrated for this invention that the deletion of the respective histidine in the $E^{RNS}$ of a BVD pestivirus (position 349, numbered according to the sequence of BVDV CP7 GenBank/EMBL data library (accession number U63479)) results in a viable virus in which the $E^{RNS}$ glycoprotein has lost the RNase activity. In contrast to point mutations changing one amino acid into another, a deletion mutant is generally much more stable with respect to revertants. Infection of pigs with a mutant of the pathogenic CSFV Alfort/Tübingen expressing $E^{RNS}$ with this deletion did not lead to fever or other typical clinical signs of CSFV infections whereas the infection with wild type virus resulted in fever, diarrhea, anorexia, apathy, depletion of B-cells and central nervous disorders. These pigs were killed in a moribund stage showing severe hemorrhages in the skin and internal organs 14 days post inoculation. The pigs infected with the mutant did neither show viremia nor B-cell depletion as tested on days 3, 5, 7, 10, 14 post infection while CSFV was easily isolated from blood samples derived from the pigs inoculated with wild type virus. The deletion mutant apparently replicated in the animals as indicated by the induction of neutralizing antibodies (see Example 3, Table 3c). The immune response to the mutant virus was sufficient to permit to survive a lethal challenge with $2\times10^5$ $TCID_{50}$ of the highly pathogenic infection with the CSFV strain Eystrup (König, 1994) which is heterologous to the Alfort strain. Moreover, the tested animals displayed no typical clinical signs for CSFV infection like fever, diarrhea, hemorrhages, B-cell depletion or anorexia after the challenge infection. This data demonstrates that infection of pigs with the deletion mutant induces an immune response sufficient for protection against a stringent challenge.

Therefore, in a most preferred embodiment, the invention relates to vaccines according to the invention, wherein said RNase activity is inactivated by the deletion of the histidine residue at position 346, as described in FIG. 1 for the CSFV Alfort strain in an exemplary manner or corresponding thereto in other strains, of said glycoprotein.

In a further most preferred embodiment, the invention relates to BVDV vaccines according to the invention, wherein said RNase activity is inactivated by the deletion of the histidine residue at position 346, as described in FIG. 1 for the CSFV Alfort strain in an exemplary manner or corresponding thereto in other BVDV strains, of said glycoprotein.

In another aspect the present invention relates to attenuated pestiviruses, wherein the RNase activity residing in glycoprotein $E^{RNS}$ is inactivated by deletions and/or mutations of at least one amino acid of said glycoprotein with the proviso that the amino acids at position 297 and/or 346 of said glycoprotein as described in FIG. 1 for CSFV are not lysine. A recombinant pestivirus, wherein amino acids at position 297 and/or 346 of said glycoprotein are lysine has been described by Hulst et al. in 1998. These particular pestiviruses demonstrated cytopathic effects in swine kidney cells. Up to now, there has been total unawareness of the surprising and innovative attenuating feature due to the inactivation of the $E^{RNS}$ enzymatic activity.

In a preferred embodiment for the reasons stated above for vaccines the present invention also relates to pestiviruses according to the invention, wherein said RNase activity is inactivated by deletions and/or mutations located at the amino acids at position 295 to 307 and/or position 338 to 357, as described in FIG. 1 for the CSFV Alfort strain in an exemplary manner or corresponding thereto in other strains, of said glycoprotein.

In a more preferred embodiment for the reasons stated above for vaccines the present invention also relates to pestiviruses of the invention, wherein said RNase activity is inactivated by deletion or mutation of the amino acid at position 346, as described in FIG. 1 for the CSFV Alfort strain in an exemplary manner or corresponding thereto in other strains, of said glycoprotein.

In a most preferred embodiment for the reasons stated above for vaccines the present invention also relates to pestiviruses, wherein said RNase activity is inactivated by the deletion of the histidine residue at position 346, as described in FIG. 1 for the CSFV Alfort strain in an exemplary manner or corresponding thereto in other strains, of said glycoprotein.

In a further most preferred embodiment, the present invention relates to BVDV pestiviruses, wherein said RNase activity is inactivated by the deletion of the histidine residue at position 346, as described in FIG. 1 for the CSFV Alfort strain in an exemplary manner or corresponding thereto in other BVDV strains, of said glycoprotein.

The attenuated pestiviruses and active components of the vaccines of the present invention can easily be prepared by nucleic acid-modifying recombinant techniques resulting in the expression of a mutant amino acid sequence in glycoprotein $E^{RNS}$. Therefore, a further aspect of the present invention relates to nucleic acids coding for a glycoprotein $E^{RNS}$, wherein the RNase activity residing in said glycoprotein is inactivated by deletions and/or mutations of at least one amino acid of said glycoprotein with the proviso that the amino acids at position 297 and/or 346 of the glycoprotein as described in FIG. 1 for the CSFV Alfort strain are not lysine.

In a preferred embodiment the present invention relates, for reasons as mentioned above, to nucleic acids according to the invention, wherein said RNase activity is inactivated by deletions and/or mutations that are located at the amino acids at position 295 to 307 and/or position 338 to 357, as described in FIG. 1 for the CSFV Alfort strain in an exemplary manner or corresponding thereto in other strains, of said glycoprotein.

In a more preferred embodiment the present invention relates, for reasons as mentioned for vaccines, to nucleic acids according to the invention, wherein said RNase activity is inactivated by deletion or mutation of the amino acid at position 346, as described in FIG. 1 for the CSFV Alfort strain in an exemplary manner or corresponding thereto in other strains, of said glycoprotein.

In a most preferred embodiment the present invention relates to nucleic acids according to the invention, wherein said RNase activity is inactivated by the deletion of the histidine residue at position 346, as described in FIG. 1 for the CSFV Alfort strain in an exemplary manner or corresponding thereto in other strains, of said glycoprotein.

In a further most preferred embodiment the present invention relates to BVDV nucleic acids according to the invention, wherein said RNase activity is inactivated by the deletion of the histidine residue at position 346, as described in FIG. 1 for the CSFV Alfort strain in an exemplary manner or corresponding thereto in other BVDV strains, of said glycoprotein.

Nucleotides, e.g. DNA or RNA, are also useful for preparing DNA-, RNA- and/or vector-vaccines. In these vaccines, the nucleotides are applied directly to the animal or indirectly via vectors other than the original virus. Nucleotide vaccines and vector vaccines are well known from the present state of the art and will not be elaborated further.

In a further aspect, the present invention relates to the use of nucleic acids of the present invention for preparing nucleotide- and/or vector-vaccines.

The vaccines, attenuated pestiviruses, and/or nucleic acids according to the invention are particularly useful for the preparation of a pharmaceutical composition.

In consequence, a further aspect of the present invention relates to pharmaceutical compositions comprising a vaccine according to the invention, and/or a pestivirus according to the invention, and/or a nucleotide sequence according to the invention. One non-limiting example of such a pharmaceutical composition, solely given for demonstration purposes, could be prepared as follows: Cell culture supernatant of an infected cell culture is mixed with a stabilizer (e.g. spermidine and/or BSA (bovine serum albumin)) and the mixture is subsequently lyophilized or dehydrated by other methods. Prior to vaccination, said mixture is then rehydrated in aquous (e.g. saline, PBS (phosphate buffered saline)) or non-aquous solutions (e.g. oil emulsion, aluminum-based adjuvant).

An additional aspect of the present invention relates to a method of attenuation for pestiviruses. The invention provides a unique and unexpected method for attenuating pestiviruses characterized in that the RNase activity residing in glycoprotein $E^{RNS}$ is inactivated.

The specifically attenuated pestiviruses are especially useful for the preparation of vaccines. Therefore, in a further additional aspect the present invention relates to methods for producing a specifically attenuated pestivirus vaccine characterized in that the Rnase activity residing in glycoprotein $E^{RNS}$ is inactivated.

The inactivation of the RNase activity residing in glycoprotein $E^{RNS}$ provides a surprising and new method for detectably labeling pestiviruses. In a further aspect the present invention provides a method for detectably labeling pestiviruses characterized in that the RNase activity residing in glycoprotein $E^{RNS}$ is inactivated. The feature of absence of RNase activity residing in the glycoprotein $E^{RNS}$ of pestiviruses of the invention now enables for detectably labeling these pestiviruses. Labeled and unlabeled pestiviruses or the $E^{RNS}$ secreted from pestivirus infected cells in body fluids can clearly be distinguished by the absence or presence of RNase activity of the glycoproteins $E^{RNS}$ upon isolation and assaying such enzymatic activity.

For pestiviruses inactivated in their RNase activity residing in glycoprotein $E^{RNS}$ by deletion and/or mutation, a number of other techniques can be used. Such pestiviruses can easily be detected because of the structural consequences resulting from such deletions and/or mutations. For example, the sequence difference of the nucleic acid sequence of altered glycoprotein $E^{RNS}$ is detectable by nucleic acid sequencing techniques or PCR-techniques (polymerase-chain reaction) as demonstrated in example 8; the altered protein sequence can be detected by specific monoclonal antibodies, that do not recognize unaltered proteins. Vice versa, it is also possible to detect the altered and thereby structurally labeled proteins by the absence of binding to specific monoclonal antibodies that recognize unaltered glycoproteins $E^{RNS}$ under the proviso that the presence of pestiviruses can be established otherwise. And, of course, the deletions and/or mutations abrogating the RNase activity in the labeled viruses will result in different immune responses in animals when compared to the responses resulting from unlabeled pestivirus infections.

A preferred embodiment for all aspects referring to methods for attenuating pestiviruses, methods for producing a specifically attenuated pestivirus vaccine and methods for detectably labeling pestiviruses according to the invention are those methods relating to the inactivation of the glycoprotein $E^{RNS}$, wherein said RNase activity is inactivated by deletions and/or mutations of at least one amino acid of said glycoprotein.

A more preferred embodiment for all aspects referring to methods for attenuating pestiviruses, methods for producing a specifically attenuated pestivirus vaccine and methods for detectably labeling pestiviruses according to the invention are those methods relating to the inactivation of the glycoprotein $E^{RNS}$, wherein said deletions and/or mutations are located at the amino acids at position 295 to 307 and/or position 338 to 357, as described in FIG. 1 for the CSFV Alfort strain in an exemplary manner or corresponding thereto in other strains, of said glycoprotein.

A very preferred embodiment for all aspects referring to methods for attenuating pestiviruses, methods for producing a specifically attenuated pestivirus vaccine and methods for detectably labeling pestiviruses according to the invention are those methods relating to the inactivation of the glycoprotein $E^{RNS}$, wherein said RNase activity is inactivated by deletion or mutation of the amino acid at position 346, as described in FIG. 1 for the CSFV Alfort strain in an exemplary manner or corresponding thereto in other strains, of said glycoprotein.

A most preferred embodiment for all aspects referring to methods for attenuating pestiviruses, methods for producing a specifically attenuated pestivirus vaccine and methods for detectably labeling pestiviruses according to the invention are those methods relating to the inactivation of the glycoprotein $E^{RNS}$, wherein said RNase activity is inactivated by the deletion of the histidine residue at position 346, as described in FIG. 1 for the CSFV Alfort strain in an exemplary manner or corresponding thereto in other strains, of said glycoprotein.

The present invention provides vaccines and or other pharmaceutical compositions which are particularly useful for the prophylaxis and treatment of pestivirus infections in animals. Therefore, a further aspect of the present invention relates to methods for the prophylaxis and treatment of pestivirus infections in animals characterized in that a vaccine according to the invention or another pharmaceutical composition according to the invention is applied to an animal in need of such prophylaxis or treatment.

In a further aspect the present invention provides a process for the preparation of specifically attenuated pestiviruses characterized in that the RNase activity residing in glycoprotein $E^{RNS}$ is inactivated.

In one aspect the present invention provides a process for the preparation of specifically labeled pestiviruses characterized in that the RNase activity residing in glycoprotein $E^{RNS}$ is inactivated.

A preferred embodiment for all aspects referring to a process for the preparation of specifically attenuated pestiviruses, a process for the preparation of specifically labeled pestiviruses according to the invention are those processes relating to the inactivation of the glycoprotein $E^{RNS}$, wherein said RNase activity is inactivated by deletions and/or mutations of at least one amino acid of said glycoprotein.

A more preferred embodiment for all aspects referring to a process for the preparation of specifically attenuated pestiviruses, a process for the preparation of specifically labeled pestiviruses according to the invention are those processes relating to the inactivation of the glycoprotein $E^{RNS}$, wherein said deletions and/or mutations are located at the amino acids at position 295 to 307 and/or position 338 to 357, as described in FIG. 1 for the CSFV Alfort strain in an exemplary manner or corresponding thereto in other strains, of said glycoprotein.

A very preferred embodiment for all aspects referring to a process for the preparation of specifically attenuated pestiviruses, a process for the preparation of specifically labeled pestiviruses according to the invention are those processes relating to the inactivation of the glycoprotein $E^{RNS}$, wherein said Rnase activity is inactivated by deletion or mutation of the amino acid at position 346, as described in FIG. 1 for the CSFV Alfort strain in an exemplary manner or corresponding thereto in other strains, of said glycoprotein.

A most preferred embodiment for all aspects referring to a process for the preparation of specifically attenuated pestiviruses, a process for the preparation of specifically labeled pestiviruses according to the invention are those processes relating to the inactivation of the glycoprotein $E^{RNS}$, wherein said RNase activity is inactivated by the deletion of the histidine residue at position 346, as described in FIG. 1 for the CSFV Alfort strain in an exemplary manner or corresponding thereto in other strains, of said glycoprotein.

The vaccines or other pharmaceutical compositions of the present invention are useful for the prophylaxis and treatment of pestivirus infections in animals.

Therefore, in one aspect the present invention relates to the use of a vaccine according to the invention for the prophylaxis and treatment of pestivirus infections in animals. In a further aspect the present invention relates to the use of a pharmaceutical composition according to the invention for the prophylaxis and treatment of pestivirus infections in animals.

Pestiviruses and/or nucleic acids according to the invention are useful active components of a pharmaceutical composition or a vaccine. Therefore, the present invention relates in a further aspect to the use of a pestivirus of the invention and/or a nucleic acid of the invention for the preparation of a vaccine or a pharmaceutical composition.

As mentioned above the inactivation of the RNase activity residing in glycoprotein $E^{RNS}$ provides a surprising and new method for labeling pestiviruses.

As a consequence one aspect of the present invention relates to methods for distinguishing the detectably labeled pestiviruses according to the invention from unlabeled and possibly pathogenic pestiviruses. Such methods are especially useful for tracing the efficacy of labeled pestiviruses in animals. A vaccine treated animal will prove label-positive after obtaining a sample of such animal and assaying for said label. Unlabeled animals and especially unlabeled animals that prove pestivirus positive can be immediately separated, isolated or slaughtered to remove the imminent danger of spreading the pathogenic infection to other animals.

The present invention provides a method for detectably labeling pestiviruses characterized in that the RNase activity residing in glycoprotein $E^{RNS}$ is inactivated. This feature of absence of RNase activity residing in the glycoprotein $E^{RNS}$ of pestiviruses of the invention now enables for detectably labeling these pestiviruses. As a result labeled and unlabeled pestiviruses can clearly be distinguished by the absence or presence of RNase activity of the glycoprotein $E^{RNS}$ upon isolation and assaying such enzymatic activity. The determination of presence or absence of this enzymatic activity upon obtaining a sample containing a pestivirus of interest or material thereof can be performed according to standard methods as, for example, described in Example 2 or in Hulst et al. (1994).

Therefore, in a preferred embodiment the present invention relates to a method for distinguishing pestivirus-infected animals from animals vaccinated with a specifically attenuated pestivirus according to the invention, comprising the following steps:

(1) Obtaining a sample from an animal of interest suspected of pestivirus infection or a vaccinated animal;

(2) Determining the absence or presence of RNase activity of a glycoprotein $E^{RNS}$ within said sample;

(3) Correlating the absence of RNase activity of glycoprotein $E^{RNS}$ with a vaccinated animal and correlating the presence of said activity with a pestivirus infection of said animal.

The present invention provides pestiviruses inactivated in their RNase activity residing in glycoprotein $E^{RNS}$ by deletion and/or mutation. Such pestiviruses are easily detected because of the structural consequences resulting from such deletions and/or mutations. The sequence difference of the $E^{RNS}$ gene coding for the altered glycoprotein $E^{RNS}$ is detectable by sequencing techniques or PCR-techniques. As a result, the present invention provides in a preferred embodiment a method for distinguishing pestivirus-infected animals from animals vaccinated with a specifically attenuated pestivirus according to the invention, comprising the following steps:

(1) Obtaining a sample from an animal of interest suspected of pestivirus infection or a vaccinated animal;

(2) Identifying the nucleotide sequence of a pestivirus genome or protein within said sample;

(3) Correlating the deletions and/or mutations of the $E^{RNS}$ nucleotide sequence as present in the vaccine with a vaccinated animal and correlating the absence of said deletions and/or mutations with a pestivirus infection of said animal.

Furthermore, the structural changes resulting from the altered protein sequence of the glycoprotein $E^{RNS}$ of pestiviruses of the invention can be detected by specific monoclonal or polyclonal antibodies, that do not recognize unaltered proteins.

Therefore, in a further embodiment, the present invention relates to a method for distinguishing pestivirus-infected animals from animals vaccinated with an attenuated pestivirus according to the invention, comprising the following steps:

(1) Obtaining a sample from an animal of interest suspected of pestivirus infection or a vaccinated animal;

(2) Identifying a modified $E^{RNS}$ glycoprotein of an attenuated pestivirus by the specific binding of monoclonal or polyclonal antibodies to $E^{RNS}$ glycoproteins present in said sample, said glycoproteins being modified by a method according to the invention, whereby said monoclonal or polyclonal antibodies do not bind to unmodified $E^{RNS}$ glycoproteins;

(3) Correlating the specific binding of said monoclonal or polyclonal antibodies with a vaccinated animal and correlating the absence of antibody binding to a pestivirus infection of said animal under the proviso that the presence of pestiviral material in said animal and/or said sample is established otherwise.

Vice versa, it is also possible to detect the altered and thereby structurally labeled proteins by the absence of binding to specific monoclonal or polyclonal antibodies that recognize unaltered glycoproteins $E^{RNS}$ only, if the presence of pestiviruses can be established otherwise. In a preferred embodiment the present invention relates to a method for distinguishing pestivirus-infected animals from animals vaccinated with an attenuated pestivirus according to the invention, comprising the following steps:

(1) Obtaining a sample from an animal of interest suspected of pestivirus infection or a vaccinated animal;

(2) Identifying an unmodified $E^{RNS}$ glycoprotein of a pestivirus by the specific binding of monoclonal or polyclonal antibodies to $E^{RNS}$ glycoproteins present in said sample, said glycoproteins not being modified by a method according to the invention, whereby said monoclonal or polyclonal antibodies do not bind to modified $E^{RNS}$ glycoproteins;

(3) Correlating the specific binding of said monoclonal or polyclonal antibodies with a pestivirus infection in said animal and correlating the absence of antibody binding to an vaccinated animal under the proviso that the presence of pestiviral material in said animal and/or said sample is established otherwise.

Of course, the structural modification and absence of the RNase activity in the labeled viruses of the invention will result in different immune responses in animals when compared to the responses resulting from unlabeled pestivirus infections. The pestiviruses of the invention elicit a different and distinct immune response, cellular as well as humoral, that differs from unmodified and possibly pathogenic immune responses. For example, glycoproteins $E^{RNS}$ according to the invention will result in polyclonal antibodies that are different in their binding specificity when compared to polyclonal antibodies resulting from unmodified glycoproteins. This difference in binding specificity provides a label for distinguishing animals vaccinated with pestiviruses from the invention from pestivirus field infected animals. Tests for screening sera for specific polyclonal antibodies that either bind to a wildtype epitope or a marker deletion mutation of that epitope for the purpose of differentiating infected and vaccinated animals have been described, for example for pseudorabies-infected and vaccinated pigs (Kit et al., 1991).

In a preferred embodiment the present invention relates to a method for distinguishing pestivirus-infected animals from animals vaccinated with an attenuated pestivirus according to the invention, comprising the following steps:

(1) Obtaining a sample of polyclonal antibodies from an animal of interest suspected of pestivirus infection or a vaccinated animal;

(2) Identifying any specific binding of said polyclonal antibodies to unmodified glycoprotein $E^{RNS}$ or glycoprotein $E^{RNS}$ RNS as modified according to the invention.

(3) Correlating the binding of said polyclonal antibodies to unmodified glycoprotein $E^{RNS}$ with a pestivirus infection and correlating the binding of said polyclonal antibodies to glycoprotein $E^{RNS}$ as modified according to the invention with a vaccinated.

REFERENCES

1. Baker, J. C. 1987. Bovine viral diarrhea virus: a review. J. Am. Vet. Med. Assoc. 190: 1449–1458.

2. Becher, P., König, M., Paton, D. J., Thiel, H. J., 1995, Further characterization of border disease virus isolates: evidence for the presence of more than three species within the genus pesivirus. *Virology* 209 (1), 200–206.

3. Donis, R. O., Corapi, W., and Dubovi, E. J. 1988. Neutralizing monoclonal antibodies to bovine viral diarrhea virus bind to the 56K to 58K glycoprotein. *J. Gen. Virol.* 69: 77–86.

4. Fuerst T. R. et al. 1986. Eukaryotic transient expression system based on recombinant vaccinia virus that synthesizes bacteriophage T7 RNA polymerase. Proc. Natl. Acad. Sci. 83: 8122–8126.

5. Hulst, M. M., Himes, G., Newbigin, E., Moormann, R. J. M. 1994. Glycoprotein E2 of classical swine fever virus: expression in insect cells and identification as a ribonuclease. *Virology* 200: 558–565.

6. Hulst, M. M., F. E. Panoto, A. Hooekmann, H. G. P. van Gennip., and Moormann, R. J. M. 1998. Inactivation of the RNase activity of glycoprotein $E^{ms}$ of classical swine fever virus results in a cytopathogenic virus. J. *Virol* 72: 151–157.

7. Kit, M. and S. Kit. 1991. Sensitive glycoprotein gill blocking ELISA to distinguish between pseudorabies (Aujeszky's disease)-infected and vaccinated pigs. *Veterinary Microbiology* 28:141–155.

8. Kunkel, T. A., J. D. Roberts, and R. A. Zakour. 1987. Rapid and efficient site-specific mutagenesis without phenotypic selection. *Methods Enzymol.* 154:367–392.

9. König, Matthias, 1994, Virus der klassischen Schweinepest: Untersuchungen zur Pathogenese und zur Induktion einer protektiven Immunantwort. Dissertation, Tierärztliche Hochschule Hannover, Germany.

10. Meyers, G., Rümenapf, T. and Thiel, H. -J. 1989. Molecular cloning and nucleotide sequence of the genome of hog cholera virus. Virology 171: 555–567.

11. Meyers, G., Tautz, N., Becher, P., Thiel, H. -J., & K ümmerer, B. M. 1996b. Recovery of cytopathogenic and noncytopathogenic bovine viral diarrhea viruses from cDNA constructs. *J. Virol,* 70: 8606–8613.

12. Meyers, G., Thiel, H. -J., and Rümenapf, T. 1996a. Classical swine fever virus: Recovery of infectious viruses from cDNA constructs and generation of recombinant cytopathogenic swine fever virus. *J. Virol.* 67:7088–709526.

13. Moennig, V. and Plagemann, J. 1992. The pestiviruses. Adv. Virus Res. 41: 53–91.

14. Paton, D. J., Lowings, J. P., Barrett, A. D. 1992. Epitope mapping of the gp53 envelope protein of bovine viral diarrhea virus. *Virology* 190: 763–772.

15. Pellerin, C. et. al. Identification of a new group of bovine viral diarrhea virus strains associated with severe outbreaks and high mortalities, Virology 203, 1994:260–268.

16. Rice, C. M. 1996. The pestiviruses. In *Fields Virology,* eds. Fields, B. N., Knipe, D. M., & Howley, P. M. (Lippincott-Raven, Philadelphia), pp. 931–959.

17. Rümenapf, T., Unger, G., Strauss, J. H., and Thiel, H. -J. 1993. Processing of the evelope glycoproteins of pestiviruses. J. Virol. 67: 3288–3294

18. Schneider, R., G. Unger, R. Stark, E. Schneider-Scheizer, and H. -J. Thiel. 1993. Identification of a structural glycoprotein of an RNA virus as a ribonuclease. *Science* 261: 1169–1171.

19. Thiel, H. -J., Plagemann, G. W., & Moennig, V. 1996. The pestiviruses. In *Fields Virology,* eds. Fields, B. N., Knipe, D. M., & Howley, P. M. (Lippincott-Raven, Philadelphia), pp. 1059–1073.

20. Thiel, H. -J., Stark, R., Weiland, E., Rümenapf, T. & Meyers, G. 1991. Hog cholera virus: molecular composition of virions from a pestivirus. *J. Virol.* 65: 4705–4712.31.

21. van Rijn, P. A., van Gennip, H. G., de Meijer, E. J., Moormann, R. J. 1993. Epitope mapping of envelope glycoprotein E1 of hog cholera virus strain Brescia. *J. Gen. Virol.* 74: 2053–2060.

22. Weiland, E., Thiel, H. -J., Hess, G., and Weiland, F. (1989). Development of monoclonal neutralizing antibodies agaist bovine viral diarrhea virus after pretreatment of mice with normal bovine cells and cyclophosphamide. J. Virol. Methods 24: 237–244.

23. Weiland, E., Stark, R., Haas, B., Rümenapf, T., Meyers, G. and Thiel, H. -J. (1990). Pestivirus glycoprotein which induces neutralizing antibodies forms part of a disulfide-linked heterodimer. J. Virology 64, 3563–3569.

24. Weiland, E., Ahl, R., Stark, R., Weiland, F. and Thiel, H. -J. (1992). A second envelope glycoprotein mediates neutralization of a pestivirus, hog cholera virus. J. Virology 66, 3677–3682.

25. Windisch, J. M., Schneider, R., Stark, R., Weiland, E., Meyers, G., and Thiel, H. -J. 1996. RNase of classical swine fever virus: biochemical characterization and inhibition by virus-neutralizing monoclonal antibodies. *J. Virol.* 70: 352–358

EXAMPLES

Example 1

Generation of RNase-Negative Pestivirus Mutants

Starting with the full length cDNA clones pA/CSFV (Meyers et al., 1996a) or pA/BVDV (Meyers et al., 1996b), from which infectious cRNA can be obtained by in vitro transcription, subclones were generated. For CSFV, a XhoI/SspI fragment of pA/CSFV was cloned into pBluescript SK+, cut with XhoI and SmaI. For BVDV, a XhoI/BglII fragment from pA/BVDV was cloned into plasmid pCITE-2C, cut whit the same enzymes. Single stranded plasmid DNA was produced from these constructs according to the method of Kunkel (Kunkel et al., 1987) using *E. coli* CJ 236 cells (BioRad) and the VCMS single strand phage (Stratagene). The single stranded DNA was converted to double strands using the 'Phagemid in vitro Mutagenesis Kit' (BioRad). Some of the synthetic oligonucleotides which were used as primers for generating the desired pestivirus mutants are listed below in an exemplary fashion:

```
C-297-L
(SEQ ID NO:1):    AGGAGCTTACTTGGGATCTG

C-346-L
(SEQ ID NO:2):    GGAACAAACTTGGATGGTGT

C-297-K
(SEQ ID NO:3):    ACAGGAGCTTAAAAGGGATCTGGC

C-346-K
(SEQ ID NO:4):    ATGGAACAAAAAGGGATGGTGTAA

C-346-d
(SEQ ID NO:5):    GAATGGAACAAAGGATGGTGTAAC

B-346-d
(SEQ ID NO:6):    CATGAATGGAACAAAGGTTGGTGCAACTGG
```

The double stranded plasmid DNA was used for transformation of *E. coli* XL1-Blue cells (Stratagene). Bacterial colonies harboring plasmids were isolated via ampicillin selection. Plasmid DNA was prepared and further analyzed by nucleotide sequencing using the T7 polymerase sequencing kit (Pharmacia). Plasmids containing the desired mutations and no second site changes were used for the construction of full length cDNA clones. In the case of CSFV, a XhoI/NdeI fragment from the mutagenized plasmid was inserted together with a NdeI/BglII fragment derived from plasmid 578 (pCITE 2A, containing the XhoI/BglII fragment form pA/CSFV) into pA/CSFV cut with XhoI and BglII. To obtain the BVDV CP7 mutant, a XhoI/BglII fragment containing the deletion was inserted into pA/BVDV cut with XhoI and NcoI together with a BglII/NcoI fragment isolated from pA/BVDV/Ins-. From construct pA/BVDV/Ins- a cRNA was transcribed that gives rise to a noncytopathogenic BVDV upon transfection in suitable cells (Meyers et al., 1996b).

The different full length clones were amplified, and the plasmids isolated. The presence of the desired mutations was proven by DNA sequencing. After linearization with SrfI (CSFV full length clones) or SmaI (BVDV full length clones) cRNA was transcribed as described previously (Meyers et al., 1996ab). RNA was purified by gel filtration and phenol/chloroform extraction and used for transfection of porcine kidney (PK15) cells or bovine kidney (MDBK clone B2) cells (CSFV or BVDV constructs, respectively). The transfections were analyzed by immunofluorescence with virus specific antisera. In cases where the desired mutants could be recovered (immunofluorescence positive) the viruses were amplified by passage on the same cell lines used for the transfection experiments. Further analysis of the CSFV mutants included determination of one step growth curves and characterization of viral RNA by Northern blot with virus specific cDNA probes as well as reverse transcription polymerase chain reaction (RT-PCR) and subsequent sequencing of the PCR fragments to verify the presence of the desired mutations in the viral genome. In all cases the presence of the desired mutation was proven. All of the recovered viruses grew equally well and produced similar amounts of RNA just as the virus resulting from the plasmid displaying the wild type sequence.

The viability of the BVDV mutant was shown by transfection of the respective cRNA and splitting of the cells 3 days thereafter. Part of the cells was seeded into a 3.5 cm diameter dish, fixed with acetone/methanol at the day thereafter and analyzed by immunofluorescence with a mixture of BVDV-specific monoclonal antibodies (Weiland et al., 1989). All cells were found positive whereas a control of cells transfected with noninfectious RNA showed no signal. From a part of the cells transfected with the respective cRNA, an extract was produced by one cycle of freezing and thawing. Fresh cells were infected with this cell extract and proved to be BVDV positive by BVDV specific immunofluorescence 3 days post infection.

Table 1 summarizes the different changes introduced into the conserved sequences of $E^{RNS}$ representing the putative active site of the RNase which are encoded by the indicated virus mutants

TABLE 1

| Name | Sequence in RNase motif | | RNase activity | Viability of mutant |
|---|---|---|---|---|
| pA/CSFV | ...SLHGIWPEKIC... | ...RHEWNKHGWCNW.. | + | + |
| C-297-L<br>(SEQ ID NOS: 7 and 8, respectively) | ...SLLGIWPEKIC... | ...RHEWNKHGWCNW.. | − | + |
| C-346-L<br>(SEQ ID NOS: 9 and 8, respectively) | ...SLHGIWPEKIC... | ...RHEWNKLGWCNW.. | − | + |
| C-297-L/346-L<br>(SEQ ID NOS: 7 and 10, respectively) | ...SLLGIWPEKIC... | ...RHEWNKLGWCNW.. | − | + |
| C-297-K | ...SLKGIWPEKIC... | ...RHEWNKHGWCNW.. | − | + |

TABLE 1-continued

| Name | Sequence in RNase motif | | RNase activity | Viability of mutant |
|---|---|---|---|---|
| (SEQ ID NOS: 11 and 8, respectively) | | | | |
| C-346-K | ...SL<u>H</u>GIWPEKIC... | ...RHEWNK<u>K</u>GWCNW.. | − | + |
| (SEQ ID NOS: 7 and 12, respectively) | | | | |
| C-297-d | ...SL_GIWPEKIC... | ...RHEWNK<u>H</u>GWCNW.. | − | − |
| (SEQ ID NOS: 13 and 18, respectively) | | | | |
| C-346-d | ...SL<u>H</u>GIWPEKIC... | ...RHEWNK_GWCNW.. | − | + |
| (SEQ ID NOS: 7 and 14, respectively) | | | | |
| C-296/7/8-d | ...S___IWPEKIC... | ...RHEWNK<u>H</u>GWCNW.. | − | − |
| (SEQ ID NOS: 15 and 8, respectively) | | | | |
| C-345/6/7-d | ...SL<u>H</u>GIWPEKIC... | ...RHEWN___WCNW.. | − | − |
| (SEQ ID NOS: 7 and 16, respectively) | | | | |
| C-345/6-d | ...SL<u>H</u>GIWPEKIC... | ...RHEWN__GWCNW.. | − | − |
| (SEQ ID NOS: 7 and 17, respectively) | | | | |
| C-346/7-d | ...SL<u>H</u>GIWPEKIC... | ...RHEWNK__WCNW.. | − | − |
| (SEQ ID NOS: 7 and 18, respectively) | | | | |
| C-342-d | ...SL<u>H</u>GIWPEKIC... | ...RH_WNK<u>H</u>GWCNW.. | − | − |
| (SEQ ID NOS: 7 and 19, respectively) | | | | |
| C-342/6-d | ...SL<u>H</u>GIWPEKIC... | ...RH_WNK_GWCNW.. | − | − |
| (SEQ ID NOS: 7 and 20, respectively) | | | | |
| C-301-d | ...SL<u>H</u>GIW_EKIC... | ...RHEWNK<u>H</u>GWCNW.. | − | − |
| (SEQ ID NOS: 21 and 8, respectively) | | | | |
| C-295-S/G | ...GL<u>H</u>GIWPEKIC... | ...RHEWNK<u>H</u>GWCNW.. | − | + |
| (SEQ ID NOS: 22 and 8, respectively) | | | | |
| C-300-W/G | ...SL<u>H</u>GIGPEKIC... | ...RHEWNK<u>H</u>GWCNW.. | − | + |
| (SEQ ID NOS: 23 and 8, respectively) | | | | |
| C-302-E/A | ...SL<u>H</u>GIWPAKIC... | ...RHEWNK<u>H</u>GWCNW.. | − | − |
| (SEQ ID NOS: 24 and 8, respectively) | | | | |
| C-305-C/G | ...SL<u>H</u>GIWPEKIG... | ...RHEWNK<u>H</u>GWCNW.. | − | − |
| (SEQ ID NOS: 25 and 8, respectively) | | | | |
| C-300-W/G-302-E/A | ...SL<u>H</u>GIGPAKIC... | ...RHEWNK<u>H</u>GWCNW.. | − | − |
| (SEQ ID NOS: 26 and 8, respectively) | | | | |
| C-340-R/G | ...SL<u>H</u>GIWPEKIC... | ...GHEWNK<u>H</u>GWCNW.. | − | − |
| (SEQ ID NOS: 7 and 27, respectively) | | | | |
| C-343-W/G | ...SL<u>H</u>GIWPEKIC... | ...RHEGNK<u>H</u>GWCNW.. | − | − |
| (SEQ ID NOS: 7 and 28, respectively) | | | | |
| C-345-K/A | ...SL<u>H</u>GIWPEKIC... | ...RHEWNA<u>H</u>GWCNW.. | − | − |
| (SEQ ID NOS: 7 and 29, respectively) | | | | |
| C-297-K/346-K | ...SL<u>K</u>GIWPEKIC... | ...RHEWNK<u>K</u>GWCNW.. | − | + |
| (SEQ ID NOS: 11 and 12, respectively) | | | | |
| C-297-K/346-L | ...SL<u>K</u>GIWPEKIC... | ...RHEWNK<u>K</u>GWCNW.. | − | + |
| (SEQ ID NOS: 11 and 10, respectively) | | | | |
| pA/BVDV | ...SL<u>H</u>GIWPEKIC... | ...RHEWNK<u>H</u>GWCNW.. | + | + |
| (SEQ ID NOS: 7 and 8, respectively) | | | | |
| B-346-d | ...SL<u>H</u>GIWPEKIC... | ...RHEWNK_GWCNW.. | − | + |
| (SEQ ID NOS: 7 and 14, respectively) | | | | |

Legend to Table 1: Test for RNase activity was done in a transient assay. BHK21 cells were infected with Vaccina virus vTF7-3 (Fuerst et al, 1986) and then transfected with the respective cDNA construct (5 μg of plasmid DNA, transfection using Superfect as recommended by the supplier (Qiagen)). After 10 hours incubation at 37° C. in a CO$_2$ incubator, the transfected cells were lysed and processed for determination of RNase activity as described below). Viability was determined as described below.

Example 2

Effect of Different Mutations on RNase Activity of E$^{RNS}$

To test the effect of the different mutations on the RNase activity of E$^{RNS}$ appropriate cells were infected with the mutant viruses. For CSFV, the infection was carried out with a multiplicity of infection (m.o.i.) of 0.01. Infection with wild type virus served as a positive control whereas noninfected cells were used as a negative control. At 48 h post infection, cells were washed twice with phosphate buffered saline and lysed in 0.4 ml of lysis buffer (20 mM Tris/HCl; 100 mM NaCl, 1 mM EDTA, 2 mg/ml bovine serum albumin; 1% Triton X100; 0.1% deoxycholic acid; 0.1% sodium dodecyl sulfate). The lysate was given into 1.5 ml reaction tubes, sonified (Branson sonifier B12, 120 Watt, 20 s in a cup horn water bath), cleared by centrifugation (5 min, 14,000 rpm, Eppendorf Centrifuge, 4° C.) and the supernatant subjected to ultracentrifugation (Beckmann table top ultracentrifuge, 60 min at 4° C. and 45,000 rpm in a TLA 45 rotor). Determination of RNase activity was done in a total volume of 200 μl containing 5 or 50 μl of supernatant of the second centrifugation step and 80 μg of Poly(rU) (Pharmacia) in RNase-assay buffer (40 mM Tris-acetate (pH 6.5), 0.5 mM EDTA, 5 mM dithiothreitol (DTT)). After incubation of the reaction mixture at 37° C. for 1 hour 200 μl of 1.2 M perchloric acid, 20 mM LaSO$_4$ was added. After 15 min incubation on ice the mixture was centrifugated for 15 min at 4° C. and 14,000 rpm in an Eppendorf centrifuge. To the supernatant 3 volumes of water were added and an aliquot of the mixture was analyzed by measuring the optical density at 260 nm using an Ultrospec 3000 spectrophotometer (Pharmacia). In all cases, the mutations introduced into the E$^{ms}$ gene completely abrogated RNase activity (Table 1).

For the BVDV mutant RNase activity was tested with material obtained after RNA transfection without passage of the recovered viruses. Cells transfected with the appropriate RNA were split 72 h post transfection and seeded in two dishes. 24 h later, from one dish, cell extracts were prepared and analyzed for RNase activity as described above. To prove infection, the cells of the second dish were analyzed by immunofluorescence with BVDV specific monoclonal antibodies (Weiland et al., 1989) and found 100% positive. Transfection was carried out with RNA transcribed from pA/BVDV/Ins- and from pA/B-346-d, the plasmid equivalent to pA/BVDV/Ins- but containing the deletion of the codon equivalent to the codon 346 in the CSFV Alfort genome. Nontransfected MDBK cells served as a negative control.

host, animal experiments were conducted with mutant V(pA/C-346-d) (C346-d in tables). Virus recovered from the CSFV full length clone without mutation (V(pA/CSFV)) served as a positive control (C-WT in tables). For each mutant three piglets (breed: German landrace; about 25 kg body weight) were used. The infection dose was $1\times10^5$ $TCID_{50}$ per animal; two thirds of the inoculate was administered intranasally (one third in each nostril), one third intramuscularly. The two groups were housed in separate isolation units. Blood was taken from the animals two times before infection and on days 3, 5, 7, 10, 12 and 14. In

TABLE 2A

Determination of RNase activity of different viruses

|  | Alfort | C-WT | C-297-L | C-346-L | C-346-d | C-346-d/Rs | control |
|---|---|---|---|---|---|---|---|
| $OD_{260}$ | 2.4 | 2.3 | 1.1 | 1.1 | 1.1 | 2.3 | 1.1 |
|  | Alfort | C-WT | C-297-L | C-346-L | C-297-K | C-346-K | C-297-L/346-L |
| $OD_{260}$ | 2.09 | 2.16 | 0.715 | 0.77 | 0.79 | 0.766 | 0.77 |
|  | C-297-K/346-L | | C-297-K/346-K | | C-346-d | | Control |
| $OD_{260}$ | 0.725 | | 0.835 | | 0.8 | | 0.84 |

Description of TABLE 2A:
PK15 cells were infected with the indicated viruses at an m.o.i. (multiplicity of infection) of 0.01, incubated at 37° C. for 48 h in a $CO_2$ incubator, and then lysed and subjected to RNase test. The acid soluble RNA resulting from incubation with the different cell extracts was quantified by measuring the optical density at 260 nm. The observed differences in RNase activity were not due to different amounts of $E^{RNS}$ protein in the samples since similar values were obtained after quantification of $E^{RNS}$ by radioactive labeling, immunoprecipitation and analysis of radioactivity with a phosphorimager. Moreover, reduction of the $E^{rns}$ concentration in the assay down to only one tenth of the usual amount did not change the resulting OD values considerably, indicating that with the chosen conditions the assay was saturated with $E^{rns}$.
CSFV strain Alfort; all other viruses were recovered from RNA transcribed in vitro from plasmids: e.g. C-WT from pA/CSFV; C-297-L from pA/C-297-L; etc.; C-346-d/Rs virus was recovered from pA/C-346-d/Rs (generated by reversion of mutation in pA/C-346-d by exchange of the respective cDNA fragment against the equivalent fragment derived from pA/CSFV); control: extract of non-infected PK15 cells.

TABLE 2B

|  | B-WT | B-346-d | control |
|---|---|---|---|
| $OD_{260}$ | 2.5 | 1.1 | 1.1 |

Description of TABLE 2B
MDBK cells were infected with in vitro transcribed RNA, split 72 h post transfection and analyzed 24 h later for RNase activity. Infection of the cells was proven by immunofluorescence analysis as described in the text. B-WT: virus recovered from pA/BVDV/Ins-; B-346-d: virus recovered from pA/B-346-d; control; extract from noninfected MDBK cells.

Example 3

Pathogenicity of CSFV After RNase Inactivation

To test, whether the destruction of the RNase activity influences the pathogenicity of pestiviruses in their natural addition, temperature was recorded daily (FIG. 2). The animals infected with the wild type virus showed typical symptoms of classical swine fever like fever, ataxia, anorexia, diarrhea, central nervous disorders, hemorrhages in the skin (Table 3a). Virus could be recovered form the blood on days 3 (animal #68) and on days 5, 7, 10, 14 (animals #68, #78, #121) (Table 3b) The animals were killed in a moribund stage at day 14 post infection. At this time, no virus neutralizing antibodies could be detected. In contrast, the animals infected with the mutant did not develop clinical symptoms (Table 3a). The temperature stayed normal (FIG. 2) over the whole experimental period and the animals never stopped taking up food. At no time virus could be recovered from the blood. Nevertheless, the animals were clearly infected and the virus most likely replicated since all animals developed neutralizing antibodies (Table 3c).

TABLE 3a

Clinical signs after test infection:

Animal experiment 1 clinical signs

| Anim. No.: | infected with | fever | diarrhea | CNS disorders | anorexia | hemorrhages in skin | apathia | moribund at day of euthanasia | Hemorrhages in organs at necropsy |
|---|---|---|---|---|---|---|---|---|---|
| #68 | C-WT | + | + | + | + | + | + | + | + |
| #78 | C-WT | + | + | + | + | + | + | + | + |

TABLE 3a-continued

Clinical signs after test infection:

Animal experiment 1 clinical signs

| Anim. No.: | infected with | fever | diar-rhea | CNS disorders | ano-rexia | hemor-rhages in skin | apathia | moribund at day of euthanasia | Hemorrhages in organs at necropsy |
|---|---|---|---|---|---|---|---|---|---|
| #121 | C-WT | + | + | + | + | + | + | + | + |
| #70 | C-346-d | − | − | − | − | − | − | − | n.a. |
| #72 | C-346-d | − | − | − | − | − | − | − | n.a. |
| #74 | C-346-d | − | − | − | − | − | − | − | n.a. |

Description of TABLE 3a:
6 piglets (German land race; about 25 kg body weight) in two groups (each group was housed separately) were included in the study. 3 animal were infected with CSFV-WT ($1 \cdot 10^5$ TCID$_{50}$) and 3 animals with C-346-d ($1 \cdot 10^5$ TCID$_{50}$). Rectal temperature and clinical signs were recorded and summarized as detailed in the table; n.a.: no necropsy was performed.

TABLE 3b

Blood cell viremia after test infection
Animal experiment 1

| Animal number | infected with | viremia at days post infection | | | | |
|---|---|---|---|---|---|---|
| | | 3 | 5 | 7 | 10 | 14 |
| #68 | C-WT | + | + | + | + | + |
| #78 | C-WT | − | + | + | + | + |
| #121 | C-WT | − | + | + | + | + |
| #70 | C-346-d | − | − | − | − | − |
| #72 | C-346-d | − | − | − | − | − |
| #74 | C-346-d | − | − | − | − | − |

Description of TABLE 3b:
Blood cell viremia was detected by cocultivation of blood with PK15 cells. After incubation at 37° C. for 72 h cells were washed with PBS, fixed with ice cold acetone/methanol and analyzed for infection by immunofluorescence with a monoclonal antibody specific for glycoprotein E2 (mAb A18, Weiland et al. 1990).

TABLE 3c

Development of CSFV specific serum neutralization titer

| days p.i. | −3 | 0 | 17 | 25 | 69 | 76 | 79 | 87 |
|---|---|---|---|---|---|---|---|---|
| pig #70 | — | — | 1:18 | 1:162 | 1:162 | 1:162 | 1:486 | 1:1458 |
| pig #72 | — | — | 1:18 | 1:54 | 1:486 | 1:1458 | 1:1458 | 1:4374 |
| pig #74 | — | — | 1:6 | 1:54 | 1:162 | 1:162 | 1:486 | 1:1458 |

Description of TABLE 3c:
Antibody titers of pigs infected with virus mutant C-346-d determined at different time points during the animal experiment:
50 µl of the diluted serum were mixed with 50 µl of medium containing 30 TCID$_{50}$ of virus (CSFV Alfort/Tübingen). After 90 minutes incubation at 37° C., 100 µl of cells ($1.5 \times 10^4$ cells) were added and the mixture was seeded in 96 well plates. After 72 h the cells were fixed with ice cold acetone/methanol and analyzed for infection by immunofluorescence with a monoclonal antibody specific for glycoprotein E2 (mAb A18, Weiland et al. 1990). On day 69 post infection the animals were challenged with $2 \times 10^5$ TCID$_{50}$ of CSFV strain Eystrup. The table gives the highest serum dilution resulting in complete neutralization of input virus.

Example 4

Induction of Protective Immunity by Infection With RNase Negative Virus

To analyze whether the infection with the mutant virus had led to a protective immunity, a challenge experiment was conducted about 9 weeks after the infection with the CSFV mutant using a highly pathogenic heterologous CSFV strain (strain Eystrup, originated from Behring). $2 \times 10^5$ TCID$_{50}$ of virus was used for the infection. This amount of virus was found to be sufficient to induce lethal disease in several preceeding experiments (König, 1994). However, the animals previously infected with the CSFV RNase mutant did not show symptoms of disease after challenge infection. Neither fever (FIG. 3) nor viremia could be detected but an increase in neutralizing antibodies indicated productive infection and replication of the challenge virus.

Example 5

Confirmation of Attenuation Principle

To show, that the observed attenuation of the mutant virus is indeed due to the deletion of the histidine at position 346 of the polyprotein and not a consequence of an unidentified second site mutation, the wild type sequence was restored by exchange of a 1.6 kb XhoI/NdeI fragment of the full length clone pA/C-346-d against the corresponding fragment of pA/CSFV displaying the wild type sequence. The fragment excised from pA/C-346-d was analyzed by nucleotide sequencing for mutations. Except for the deletion of the triplet coding for histidine 346 of the polyprotein, no difference with regard to the wild type sequence was found. From the cDNA construct with the rescued mutant, virus V(pA/C-346-d/Rs) could be recovered that grew equally well as wild type virus and showed equivalent RNase activity (Table 2A).

In a second animal experiment, the rescued virus was used for infection of pigs. As a control, the deletion mutant was used. Again, two groups consisting of three animals were used. As the animals were younger (German landrace, about 20 kg) than those in the first experiment, $5 \times 10^4$ TCID$_{50}$ of virus were used for infection this time. Again, the animals infected with the mutant showed no clinical signs (Table 5, FIG. 4). Only one animal had fever for one day. Nevertheless, these animals developed neutralizing antibodies and were protected against a lethal CSFV challenge. Challenge was again performed by infection with $2 \times 10^5$ TCID$_{50}$ of challenge strain Eystrup. The animals did not show clinical signs after challenge and the temperature stayed normal (FIG. 5). In contrast to the pigs infected with the deletion mutant, the animals inoculated with the rescued wild type virus developed fatal classical swine fever. One animal had to be killed 11 days after infection, the other two 3 days later. All animals showed typical symptoms of classical swine fever, i.e. fever, diarrhea, annorexia, and pathological signs like hemorrhages in different organs including the kidney.

6). For all animals virus was recovered from the blood on day 5 whereas no viremia was detected at later time points (Table 6a). All animals developed neutralizing antibodies TABLE 5a Clinical signs after test infection Animal experiment 2

| Anim. No.: | infected with | fever | diarrhea | CNS disorders | anorexia | hemor- rhages in skin | apathia | moribund at day of euthanasia | hemorrhages in organs at necropsy |
|---|---|---|---|---|---|---|---|---|---|
| #43 | C-346-d | +* | − | − | − | − | − | − | n.a. |
| #47 | C-346-d | − | − | − | − | − | − | − | n.a. |
| #87 | C-346-d | − | − | − | − | − | − | − | n.a. |
| #27 | C-346-d/RS | + | + | + | + | − | + | + | + |
| #28 | C-346-d/RS | + | + | + | + | − | + | + | + |
| #30 | C-346-d/RS | + | + | + | + | − | + | + | + |

*fever for only 1 day
TABLE 5a:
6 piglets (German land race; about 20 kg body weight) in two groups (each group was housed separately under isolation conditions) were included in the study. 3 animal were infected with mutant C-346-d ($5 \cdot 10^4$ TCID$_{50}$) and 3 animals with C-346-d/RS ($5 \cdot 10^4$ TCID$_{50}$). C-346-d/RS was derived from mutant C-346-d by restoring the wild type sequence of E$^{RNS}$ gene. Rectal temperature and clinical signs were recorded and summarized; n.a.: no necropsy was performed.

TABLE 5b

Diagnostic RNAse test with viruses recovered from infected animals during viremia

| | Alfort | animal #3 C-297-K | animal #5 C-297-K | animal #27 C-346-d/RS | animal #28 C-346-d/RS | animal #30 C-346-d/RS | Con- trol |
|---|---|---|---|---|---|---|---|
| OD$_{260}$ | 1.84 | 0.60 | 0.56 | 1.84 | 1.93 | 1.94 | 0.49 |

Viruses recovered form the blood of animals 3 and 5 at day 5 post infection and of animals 27, 28 and 30 of animal experiment #2 (described in example 5) at day 7 post infection were propagated in tissue culture, titrated and tested for RNase activity as described above. Non-infected PK15 cells and cells (control) infected with wild type CSFV (Alfort) served as controls. Animals 3 and 5 had been infected with mutant C-297-K, whereas animals 27, 28 and 30 had been infected with mutant C-346-d/RS, as indicated in the table.

Example 6

Effects of Double Mutation Within E$^{RNS}$

To test the effects of a double mutation within E$^{RNS}$ on the ability of the respective virus to replicate in its natural host and on pathogenicity, an animal experiment was conducted with mutant V(pA/C-297-L/346-L). Virus recovered from the CSFV full length clone without mutation (V(pA/CSFV) served as a positive control. For each mutant three piglets (breed: German land race; about 25 kg body weight) were used. The infection dose was $1 \times 10^5$ TCID$_{50}$ per animal; two thirds of the inoculate was administered intra-nasally (one third in each nostril), one third intramuscularly. Blood was taken from the animals before infection (day 0) and on days 5, 8, 12 and 20. In addition, temperature was recorded daily (FIG. 6). The animals infected with the double mutant did not develop any clinical symptoms, and the animals never stopped taking up food. The animals showed no fever over the whole experimental period (animals 45/2 and 45/3) except animal 45/1 on day 8, probably due to bacterial infection caused by injury of the right hind leg. After treatment of this animal with an antibiotic on day 10, temperature returned to normal values within one day (FIG.

6). For all animals virus was recovered from the blood on day 5 whereas no viremia was detected at later time points (Table 6a). All animals developed neutralizing antibodies (Table 6b). For animal 45/1 the neutralization titer was again determined about 4.5 months p.i. and was found to be 1:4374. Thus, the infection with the double mutant resulted in long lasting immunological memory.

TABLE 6a

Test for viremia

| Days p.i. | 5 | 8 | 12 |
|---|---|---|---|
| Pig 45/I | + | − | − |
| Pig 45/II | + | − | − |
| Pig 45/III | + | − | − |

TABLE 6b

Neutralization titers

| Animal | day 0 | day 20 p.i. |
|---|---|---|
| 45/1 | − | 1:128 |
| 45/2 | − | 1:256 |
| 45/3 | − | 1:256 |

Example 7

Immunogenicity and Attenuation Principle of the BVDV Virus "B-346-d"

This experiment was designed to investigate the attenuation principle as well as the immunogenicity of the BVDV virus ‚B-346-d' recovered from pA/B-346-d by comparing it with the ‚B-WT' virus recovered from pA/BVDV/Ins-. The virus ‚B-346-d' is of course mutated in original BVDV position 349 but named "B-346" to indicate the position relative to the CSFV Alfort position 346 of FIG. 1.

Three groups of BVDV seronegative animals of 3–6 months of age were selected. Groups 1 and 2 comprised 5 animals each while group 3 comprised 3 animals. Animals of group 1 and 2 were infected by administration of $2 \times 10^6$ TCID$_{50}$ of B-346-d (group 1) or B-WT (group 2) in a volume of 5 ml per route. Animals were infected intra-muscularly (gluteal muscle), intranasally and subcutaneously (over scapula). Over a period of 14 days after infection, viremia in both groups was monitored through parameters like blood cell viremia and virus shedding in nasal swabs. In addition, clinical parameters like rectal temperatures, white blood cell counts and general health parameters were monitored.

The protective immunity against an infection with an antigenetically heterologous and virulent BVDV-isolate (#13) was investigated by challenge infection 77 days after infection of the animals of group 1 with B-346-d. Animals of group 3 served as challenge control and were infected according to the procedure for the animals of group 1 with the virulent BVDV-isolate. The BVDV virus (#13) belongs to a different antigenetic group (type II), whereas the B-346-d virus belongs to the antigenetic group (type I) according to the classification described by (Pellerin, C. et. al., 1994). Animals of group 1 and 3 got infected by administration of $2 \times 10^6$ TCID$_{50}$ of BVDV isolate (#13) in a volume of 5 ml per route. Animals were infected via the intra-muscular (gluteal muscle), intra-nasal and subcutaneous route (over Scapula). Over a period of 14 days after infection viremia in both groups was monitored by parameters like blood cell viremia and virus shedding in nasal swabs. In addition, clinical parameters like rectal temperatures, white blood cell counts and general health parameters were monitored.

After infection with B-346-d animals did not show any typical clinical symptoms of a BVDV infection such as rectal temperature increase (Table 7a), or any respiratory clinical symptoms (not shown).

The reduced blood cell viremia (Table 7b) and virus shedding in nasal swabs (Table 7c) did clearly indicate an attenuation of B-346-d compared to B-WT.

The virulent BVDV isolate #13 did induce in the animals of group 3 a strong viremia with typical signs of a BVDV infection, like rectal temperature increase over a period of several days (Table 7d), strong leucopenia (Table 7e), extended blood cell viremia (Table 7f) and virus shedding in nasal swab fluid (Table 7g). In contrast, animals of group 1, which had been vaccinated by infection with B-346-d, did show almost no clinical symptoms typical for a BVDV infection after the challenge infection with the virulent BVDV isolate #13. There was no significant increase in rectal temperatures after infection (Table 7d). The observed leucopenia was very marginal with regard to magnitude and duration (Table 7e). No BVDV could be isolated from the blood (Table 7f) and for only one animal virus shedding in nasal swab exudate could be detected (Table 7g).

Therefore, infection with B-346-d induces a strong immunity which clearly reduces clinical signs, virus shedding and blood cell viremia after challenge infection with a heterologous BVDV isolate.

TABLE 7a

Mean rectal temperatures in group 1 (B-346-d) and 2 (B-WT)

| Day of study: | 0 | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|
| Group 1 | 38.8 | 39.1 | 39.0 | 38.7 | 38.8 | 38.7 | 38.7 | 38.5 | 38.7 | 38.5 | 38.5 | 38.5 | 38.4 | 38.9 | 38.7 |
| Group 2 | 38.8 | 39.0 | 38.9 | 38.6 | 38.6 | 38.7 | 38.6 | 38.4 | 39.1 | 38.4 | 38.7 | 38.6 | 38.7 | 38.6 | 38.6 |

Animals of group 1 were infected at day 0 with $6 \times 10^6$ TCID$_{50}$ B-346-d, whereas animals of group 2 were infected with $6 \times 10^6$ TCID$_{50}$ B-WT.

FIG. 7b

Blood cell viremia of groups 1 and 2

| Group | Animal | First day nasal shedding recorded | Final day nasal shedding recorded | Recorded duration of nasal shedding (days) | Mean duration of group (days) |
|---|---|---|---|---|---|
| 1 | 1 | 6 | 6 | 1 | 1.4 |
|   | 2 | 4 | 6 | 2 |   |
|   | 3 | 5 | 5 | 1 |   |
|   | 4 | — | — | 0 |   |
|   | 5 | 6 | 9 | 3 |   |
| 2 | 6 | 4 | 8 | 5 | 4.4 |
|   | 7 | 4 | 7 | 4 |   |
|   | 8 | 4 | 7 | 4 |   |
|   | 9 | 4 | 7 | 4 |   |
|   | 10 | 4 | 8 | 5 |   |

EDTA blood was sampled daily up to day 10 post infection with B-346-d and B-WT, respectively. 2.0 ml of blood were added to each of 3 cultures of calf testis (Cte) cells with medium containing heparin (1 unit/ml to prevent clotting). After overnight incubation inoculum/medium was replaced with fresh medium without heparin. After incubation for 4 to 6 days, BVDV infected cells were detected by immunefluorescence with a polyclonal serum specific for BVDV. Negative cultures were frozen and subsequently thawed. 0.2 ml thereof were passed to a second passage on Cte cells to confirm the absence of BVDV.

TABLE 7c

Virus shedding in nasal fluid:

| Group | Animal | First day nasal shedding recorded | Final day nasal shedding recorded | Number of days virus detected in exudate | Mean number of days detected virus per group |
|---|---|---|---|---|---|
| 1 | 1 | 4 | 8 | 4 | 2.6 |
|   | 2 | 6 | 6 | 1 |   |
|   | 3 | 4 | 4 | 1 |   |
|   | 4 | 5 | 7 | 3 |   |
|   | 5 | 3 | 6 | 4 |   |
| 2 | 6 | 6 | 8 | 3 | 3.6 |
|   | 7 | 5 | 7 | 3 |   |
|   | 8 | 5 | 8 | 4 |   |
|   | 9 | 5 | 6 | 2 |   |
|   | 10 | 3 | 9 | 6 |   |

Nasal exudate was centrifuged (1000 g) to remove gross debris and contaminants. Supernatant fluid was removed and 0.2 ml were seeded to each of three cell cultures. After overnight incubation the inoculum/medium was replaced with 2 ml of fresh medium. After incubation for 4–6 days, BVDV infected cells were detected by immunofluorescence with a polyclonal serum specific for BVDV.

EDTA blood was sampled daily up to day 10 post challenge. 0.2 ml of blood were added to each of 3 cultures of calf testis (Cte) cells with medium containing heparin (1 unit/ml to prevent clotting). After overnight incubation inoculum/medium was replaced with fresh medium without heparin. After incubation for 4 to 6 days cells BVDV

TABLE 7d

Mean rectal temperatures in groups 1 and 3

| Day of study: | −2 | −1 | 0 | 1 | 2 | 3 | 4 | 5 | 6 | 7 | 8 | 9 | 10 | 12 | 14 |
|---|---|---|---|---|---|---|---|---|---|---|---|---|---|---|---|
| Group 1 | 38.4 | 38.6 | 38.5 | 38.5 | 38.6 | 38.4 | 38.4 | 38.4 | 38.3 | 38.4 | 38.4 | 38.4 | 38.4 | 38.4 | 38.5 |
| Group 3 | 38.8 | 39.1 | 38.8 | 39.1 | 39.4 | 39.7 | 40.2 | 40.2 | 40.4 | 41.3 | 40.2 | 40.1 | 40.2 | 40.8 | 40.4 |

Rectal temperatures were recorded up to 16 days after challenge infection. Animals of group 1 and 3 were infected by $6 \times 10^6$ TCID$_{50}$ of the virulent BVDV isolate #13.

TABLE 7e

Mean white blood cell counts

| Day of study: | −2 | −1 | 0 | 1 | 2 | 3 | 4 | 5 | 6 | 7 | 8 | 9 | 10 | 12 | 14 |
|---|---|---|---|---|---|---|---|---|---|---|---|---|---|---|---|
| Group 1 | 11.9 | 11.9 | 11.9 | 11.3 | 10.8 | 9.2 | 8.2 | 8.9 | 9.9 | 11.2 | 11.6 | 11.6 | 10.6 | 10.8 | 10.8 | 9.4 |
| Group 3 | 11.7 | 15.8 | 13.8 | 11.1 | 7.7 | 9.8 | 7.4 | 6.8 | 7.5 | 8.7 | 7.0 | 8.1 | 6.2 | 6.4 | 6.2 |

EDTA blood cell samples were taken daily from day −2 to 14 post challenge from each animal in both groups. Counts of white blood cells in EDTA blood samples were determined using a Sysmex Micro-Cell Counter F800.

infected cells were detected by immunefluoreszence with a polyclonal serum specific for BVDV.

Negative cultures were frozen and subsequently thawed. 0.2 ml thereof were passed to a second passage on Cte cells to confirm the absence of BVDV.

TABLE 7f

BVDV isolated from blood samples

| Group | Animal | First day virus detected in blood | Final day virus detected in blood | Recorded duration of virus in blood (days) | Mean duration (days) |
|---|---|---|---|---|---|
| 1 | 1 | — | — | 0 | 0 |
|   | 2 | — | — | 0 |   |
|   | 3 | — | — | 0 |   |
|   | 4 | — | — | 0 |   |
|   | 5 | — | — | 0 |   |
| 3 | 11 | 3 | 10 | 8 | 9.7 |
|   | 12 | 3 | 14 | 12 |   |
|   | 13 | 3 | 9 | 9 |   |

TABLE 7g

Virus shedding in nasal fluid

| Group | Animal | First day nasal shedding recorded | Final day nasal shedding recorded | Recorded duration of nasal shedding (days) | Mean duration (days, per group) |
|---|---|---|---|---|---|
| 1 | 1 | 3 | 4 | 2 | 0.8 |
|   | 2 | — | — | 0 |   |
|   | 3 | — | — | 0 |   |
|   | 4 | — | — | 0 |   |
|   | 5 | 4 | 5 | 2 |   |
| 3 | 11 | 3 | 14 | 12 | 10 |
|   | 12 | 3 | 14 | 12 |   |
|   | 13 | 3 | 8 | 6 |   |

Nasal exudate was centrifuged (1000 g) to remove gross debris and contaminants. Supernatant fluid was removed and 0.2 ml thereof were seeded to each of three cell cultures. After overnight incubation the inoculum/medium was replaced with 2 ml of fresh medium. After incubation for 4–6 days BVDV infected cells were detected by immunefluorescence with a polyclonal serum specific for BVDV.

Example 8

Discrimination Between C-346-d and CSFV Without Deletion of the Histidine Codon 346 by RT-PCR The RNA sequence coding for the conserved RNase motif in CSFV glycoprotein $E^{RNS}$ highly conserved. Among all known CSFV sequences no nucleotide exchanges were found in the region corresponding to residues 1387 to 1416 of the published sequence of the CSFV Alfort strain (Meyers et al., 1987). Thus, oligonucleotide primers derived from this conserved region of the genome can be used in an RT-PCR assay for detection of all CSFV isolates (see FIG. 7). In consequence, the absence of the triplet coding for histidine 346 (nucleotides 1399–1401) could be detected by an RT-PCR assay with an appropriately designed primer. Different oligonucleotides covering the conserved region were synthesized that either contained the histidine codon or not. These oligonucleotides served as upstream primers in RT-PCR reactions with oligonucleotide $E^{RNS}$-Stop as downstream primer. RNA purified from tissue culture cells infected with C-346-d, C-WT, C-346-L or C-346-K, respectively, were used as templates. Reverse transcription of 2 μg heat denatured RNA (2 min 92° C., 5 min on ice in 11.5 μl of water in the presence of 30 pMol reverse primer) was done after addition of 8 μl RT mix (125 mM Tris/HCl pH 8.3, 182.5 mM KCl, 7.5 mM $MgCl_2$, 25 mM dithiothreitol, 1.25 mM of each dATP, dTTP, dCTP, dGTP), 15 U of RNAguard (Pharmacia, Freiburg, Germany) and 50 U of Superscript (Life Technologies/BRL, Eggenstein, Germany) for 45 min at 37° C. After finishing reverse transcription, the tubes were placed on ice and 30 μl of PCR mix (8.3 mM Tris/HCl, pH8.3; 33.3 mM KCl; 2.2 mM $MgCl_2$; 0.42 mM of each dATP, dTTP, dCTP, dGTP; 0.17% TritonX100; 0.03% bovine serum albumine; 5 U of Taq polymerase (Appligene, Heidelberg, Germany) and 16.7% DMSO) were added. When primer Ol H+3 was used, the reaction mix for amplification contained no DMSO. Amplification was carried out in 36 cycles (30 sec 94° C.; 30 sec 57° C.; 45 sec 74° C.) 1 μl of amplification reaction was loaded on a 1% agarose gel, the amplified products were separated by electrophoresis, and stained with ethidium bromide. As demonstrated in FIG. 7, primer pair Ol H-3/Ol $E^{ms}$Stop allowed to specifically amplify a band derived from RNA containing the deletion of codon 346 whereas with the other two primer combinations products containing codon 346 were amplified and no band was observed when the RNA with the deletion of this codon was used as a template.

```
Primers for RT-PCR:

upstream:

Ol H - 3
  (SEQ ID NO:30):  TGGAACAAAGGATGGTGT

Ol H + 2
  (SEQ ID NO:31):  TGGAACAAACATGGATGG

Ol H + 3
  (SEQ ID NO:32):  GAATGGAACAAACATGGA
```

```
-continued
downstream:

Ol E^rns Stop:   GGAATTCTCAGGCATAGGCACCAAACCAGG
```

BRIEF DESCRIPTION OF THE DRAWINGS

FIG. 1: The first 495 amino acids as expressed by the Alfort strain of CSFV

The sequence listing shows the first 495 amino acids as expressed by the Alfort strain of CSFV (Meyers et al., 1989). One monomer of the glycoprotein $E^{RNS}$ of said strain corresponds to the amino acids 268 to 494 as described by Rümenapf et al. (1993). Residues 295 to 307 and 338 to 357 representing the regions showing homology to plant and fungal RNases (Schneider et al., 1993) are underlined.

Figure 2:
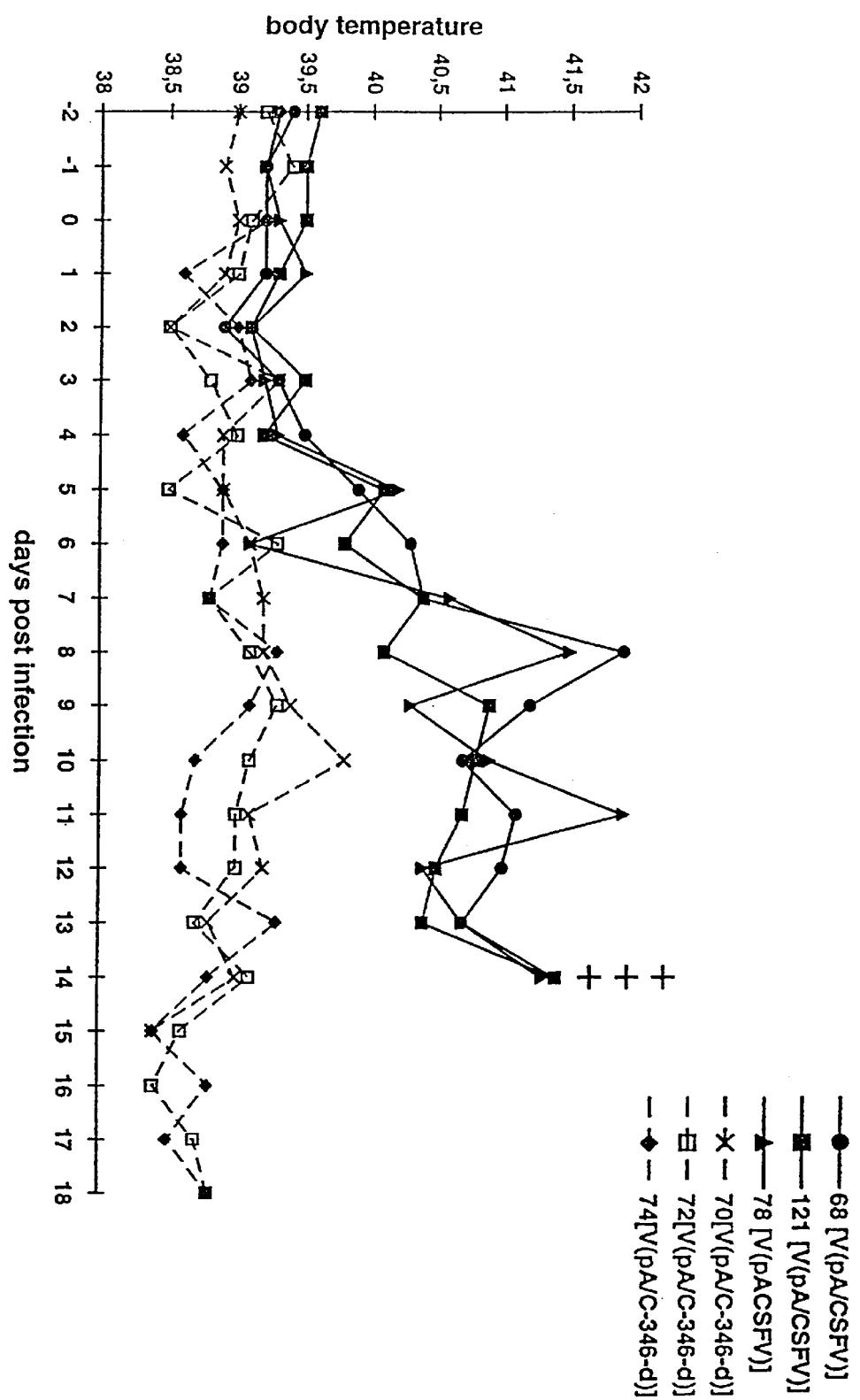

FIG. 2: Rectal temperature curve of animals after test infection

Daily rectal temperature was recorded from day 2 before till day 18 post infection. Rectal temperature curve is detailed for each animal of the group infected with the virus V(pA/CSFV) (continuous line) derived from plasmid pA/CSFV or with the virus V(pA/C-346-d) derived from plasmid pA/C-346-d (dotted line).

Figure 3:
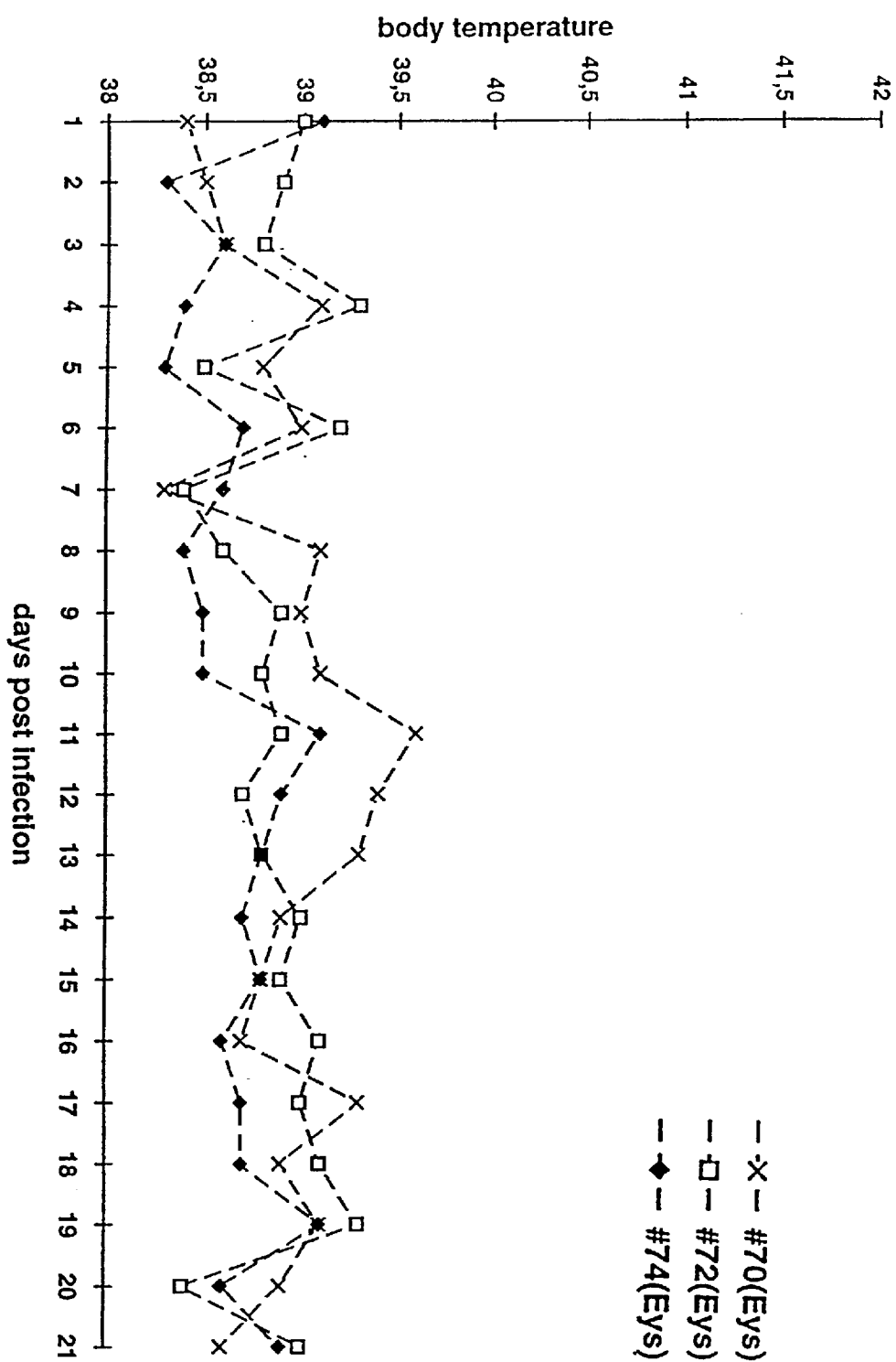

FIG. 3: Rectal temperature curve of animals after challenge infection

Figure 4:
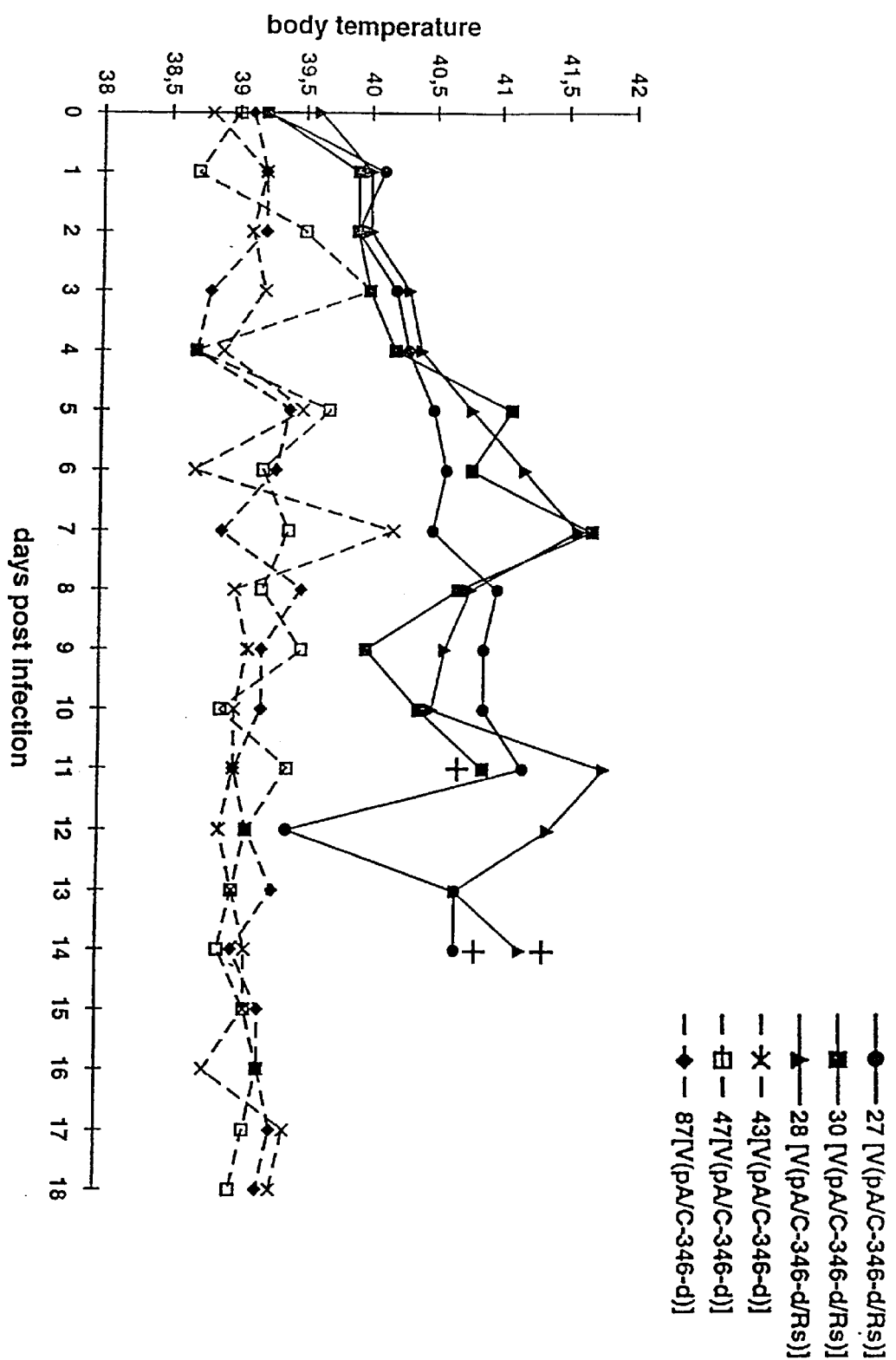

Daily rectal temperature was recorded at days 1–21 post challenge virus infection. Animals challenged with a lethal dosis of the CSFV challenge strain Eystrup had been infected with mutant C-346-d (V(pA/C-346-d)) 69 days in before as detailed in the text. Rectal temperature curve is detailed for each animal of the group challenged with $2\times10^5$ $TCID_{50}$ from the CSFV challenge strain Eystrup FIG. 4: Rectal temperature curve of animals after test infection Daily rectal temperature was recorded at days 0–18 post infection. Rectal temperature curve is detailed for each animal of the two groups infected either with C-346-d (V(pA/C-346-d)) (dotted line) or with the restored virus C-346-d/RS (V(pA/C-346-d/Rs)) (continuous line).

Figure 5:
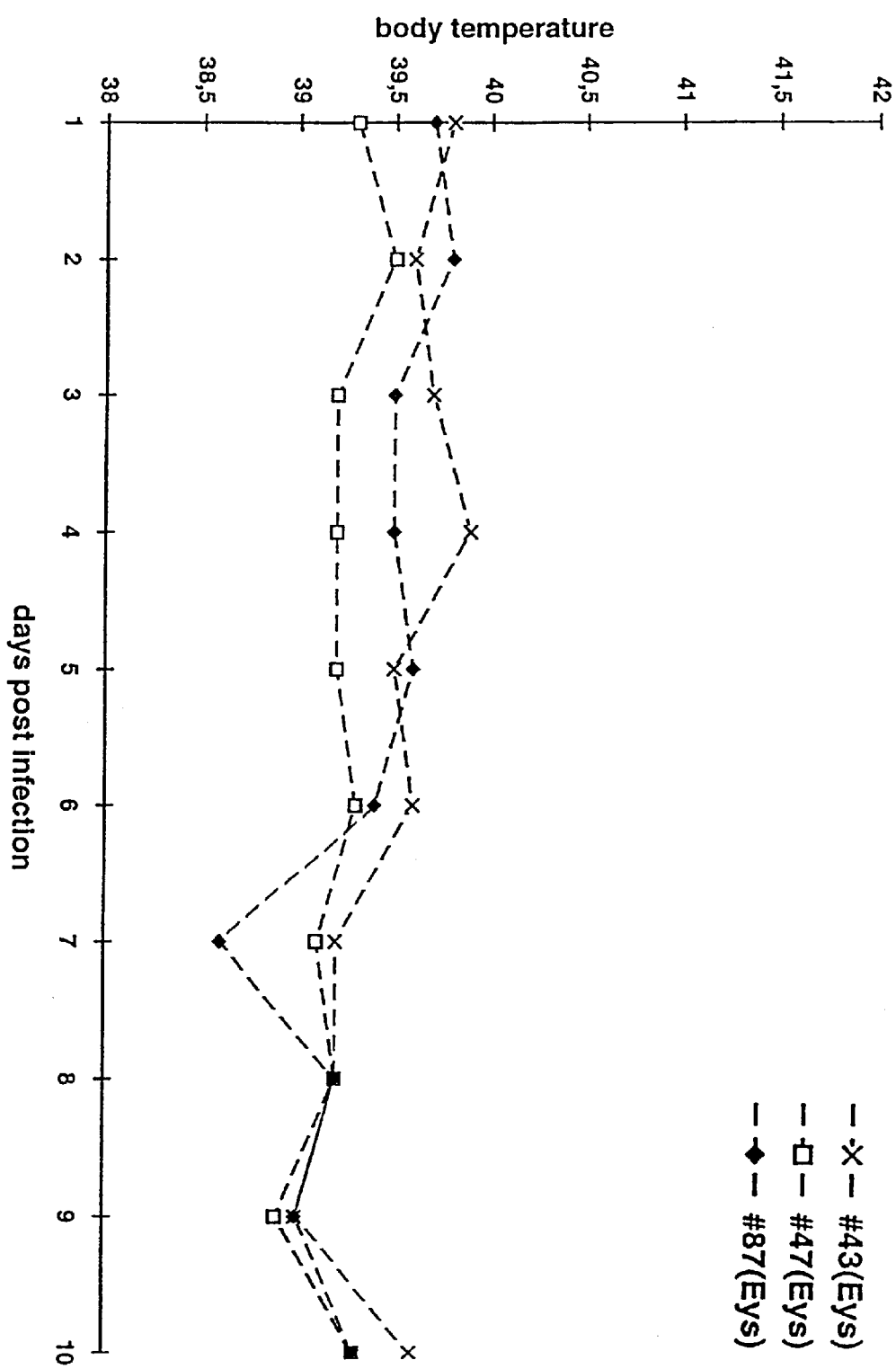

FIG. 5: Rectal temperature after challenge infection animal experiment #2

Daily rectal temperature was recorded at days 1–10 post challenge virus infection. Animals challenged with a lethal dose ($2\times10^5$ $TCID_{50}$) of the CSFV challenge strain Eystrup had been infected with mutant C-346-d 37 days in before.

Figure 6:
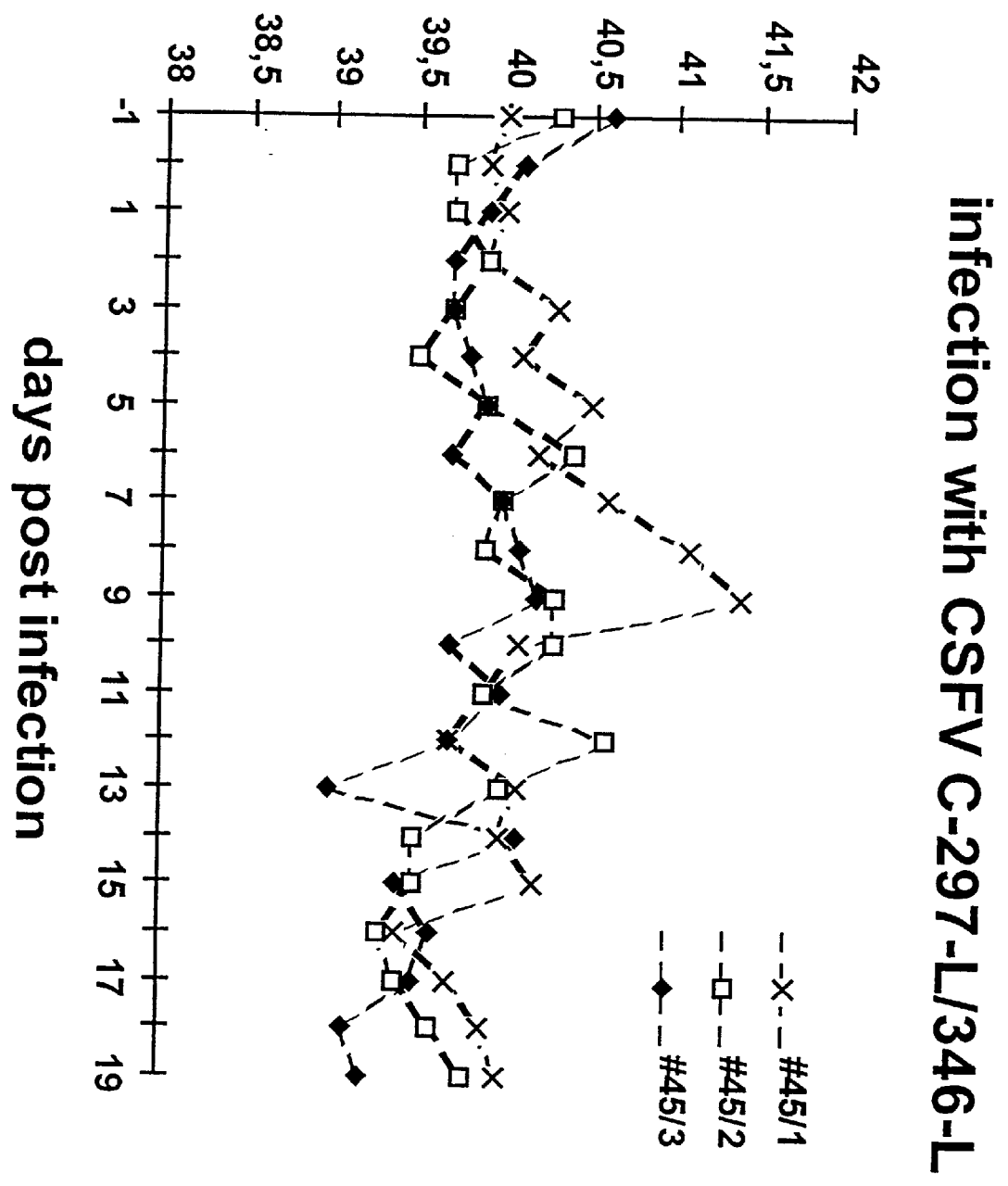

FIG. 6: Rectal temperature of animals treated with a double mutant according to example 6

Daily rectal temperature was recorded prior and post challenge virus infection with mutant V(pA/C-297-L/346-L).

FIG. 7: Discrimination between C-346-d and CSFV without deletion of the histidine codon 346 by RT-PCR according to example 8 a) Primer pair Ol H-3/01 $E^{ms}$Stop allows to specifically amplify a band derived from RNA containing the deletion of codon 346 (C-346-d) as described in detail in example 8. In contrast, RNA, not containing said deletion does not interact with said primer pair (C-WT, C-346-L, C-346-K).

b) And c) The other two primer combinations (Ol H+2 and Ol H+3) amplify bands derived from RNA that do not contain the deletion of codon 346 (Ol H+2 and Ol H+3). No band can be observed when RNA from the 346-deletion mutant C-346-d is used as a template.

I claim:

1. A purified BVDV or CSFV pestivirus, wherein the RNase activity of glycoprotein E$^{RNS}$ is inactivated by a mutation of at least one amino acid of said glycoprotein with the proviso that when said pestivirus is the CSFV pestivirus, the amino acid at position 297 or 346 of SEQ ID NO: 34 is not lysine.

2. The pestivirus of claim 1, wherein the RNase activity of glycoprotein E$^{RNS}$ is inactivated by a mutation of at least one amino acid in the active site of said glycoprotein.

3. The pestivirus of claim 1, wherein the RNase activity is inactivated by a deletion of at least one amino acid of said glycoprotein.

4. The pestivirus of claim 1, wherein said pestivirus is a CSFV pestivirus.

5. A composition comprising the pestivirus of claim 4 and a solution.

6. The composition of claim 5, which induces an immunological response in an animal.

7. The pestivirus of claim 1, wherein said pestivirus is a BVDV pestivirus.

8. A composition comprising the pestivirus of claim 7 and a solution.

9. The composition of claim 8, which induces an immunological response in an animal.

10. A composition comprising the pestivirus of claim 1 and a solution.

11. The composition of claim 10, which induces an immunological response in an animal.

12. The pestivirus of claim 1, which is a CSFV pestivirus and wherein the RNase activity of glycoprotein E$^{RNS}$ is activated by a mutation of at least one amino acid located at positions 295 to 346 of SEQ ID NO: 34.

13. A composition comprising the pestivirus of claim 12 and a solution.

14. The composition of claim 13, which induces an immunological response in an animal.

15. The pestivirus of claim 1, which is a CSFV pestivirus and wherein the RNase activity of glycoprotein E$^{RNS}$ is inactivated by a mutation of at least one amino acid located at positions 338 to 357 of SEQ ID NO: 34.

16. A composition comprising the pestivirus of claim 15 and a solution.

17. The composition of claim 16, which induces an immunological response in an animal.

18. A purified pestivirus wherein the RNase activity of glycoprotein E$^{RNS}$ is inactivated by a mutation of at least one amino acid located in the conserved E$^{RNS}$ sequence SLHGIWPEKIC.

19. The pestivirus of claim 18, wherein the RNase activity is inactivated by a deletion of at least one amino acid located in the conserved E$^{RNS}$ sequence SLHGIWPEKIC.

20. The pestivirus of claim 18, wherein said pestivirus is a CSFV.

21. The pestivirus of claim 18, wherein said pestivirus is a BVDV.

22. A composition comprising the pestivirus of claim 18 and a solution.

23. The composition of claim 22, which induces an immunological response in an animal.

24. A purified pestivirus wherein the RNase activity of glycoprotein E$^{RNS}$ is inactivated by a mutation of at least one amino acid located in the conserved E$^{RNS}$ sequence RHEWNKHGWCNW.

25. The pestivirus of claim 24, wherein the RNase activity is inactivated by a deletion of at least one amino acid located in the conserved $E^{RNS}$ sequence RHEWNKHGWCNW (SEQ ID NO: 8).

26. The pestivirus of claim 24, wherein said pestivirus is a CSFV.

27. The pestivirus of claim 24, wherein said pestivirus is a BVDV.

28. The pestivirus of claim 24, wherein said RNase activity of glycoprotein $E^{RNS}$ is inactivated by mutation of the second histidine of the conserved $E^{RNS}$ sequence RHEWNKHGWCNW.

29. The pestivirus of claim 28, wherein the RNase activity of glycoprotein $E^{RNS}$ is inactivated by the deletion of the second histidine of the conserved $E^{RNS}$ sequence RHEWNKHGWCNW.

30. The pestivirus of claim 29, wherein said pestivirus is a CSFV pestivirus.

31. The pestivirus of claim 30, wherein said CSFV pestivirus is the Alfort strain.

32. The pestivirus of claim 29, wherein said pestivirus is a BVDV pestivirus.

33. The pestivirus of claim 32, wherein said pestivirus is BVDV strain cp7.

34. A composition comprising the pestivirus of claim 32 and a solution.

35. The composition of claim 34, which induces an immunological response in an animal.

36. The composition of claim 35, which is a vaccine.

37. A composition comprising the pestivirus of claim 30 and a solution.

38. The composition of claim 37, which induces an immunological response in an animal.

39. The composition of claim 38, which is a vaccine.

40. A composition comprising the pestivirus of claim 29 and a solution.

41. The composition of claim 40, which induces an immunological response in an animal.

42. A composition comprising the pestivirus of claim 24 and a solution.

43. The composition of claim 42, which induces an immunological response in an animal.

44. A purified BVDV pestivirus, wherein the RNase activity of glycoprotein $E^{RNS}$ is inactivated by a mutation of at least one amino acid of said glycoprotein.

45. The pestivirus of claim 44, wherein the RNase activity is inactivated by a deletion of at least one amino acid of said glycoprotein.

46. The pestivirus of claim 45, wherein the RNase activity is inactivated by a deletion of at least one amino acid located in the co served $E^{RNS}$ sequence SLHGIWPEKIC.

47. The pestivirus of claim 46, wherein the RNase activity is inactivated by a deletion of at least one amino acid located in the co served $E^{RNS}$ sequence RHEWNKHGWCNW.

48. A composition comprising the pestivirus of claim 47 and a solution.

49. The composition of claim 48, which induces an immunological response in an animal.

* * * * *

UNITED STATES PATENT AND TRADEMARK OFFICE
CERTIFICATE OF CORRECTION

PATENT NO. : 7,179,473 B2
APPLICATION NO. : 09/325542
DATED : February 20, 2007
INVENTOR(S) : Meyers It is certified that error appears in the above-identified patent and that said Letters Patent is hereby corrected as shown below:

Column 44, Lines 51-52, claim 18, after "SLHGIWPEKIC", insert therein -- (SEQ ID NO:7). --.
Column 44, Line 54, claim 19, after "SLHGIWPEKIC", insert therein -- (SEQ ID NO:7). --.
Column 44, Line 65, claim 24, after "RHEWNKHGWCNW", insert therein -- (SEQ ID NO:8). --.
Column 45, Line 2, claim 25, please delete "(SEQ ID NO: 8)." and insert therein -- (SEQ ID NO:8). --.
Column 45, Line 10, claim 28, after "RHEWNKHGWCNW", insert therein -- (SEQ ID NO:8). --.
Column 45, Line 14, claim 29, after "RHEWNKHGWCNW", insert therein -- (SEQ ID NO:8). --.
Column 46, Line 20, claim 46, please delete "co served" and insert therein -- conserved --.
Column 46, Line 20, claim 46, after "SLHGIWPEKIC", insert therein -- (SEQ ID NO:7). --.
Column 46, Line 21, claim 47, please delete "46" and insert therein -- 45 --.
Column 46, Line 23, claim 47, please delete "co served" and insert therein -- conserved --.
Column 46, Line 23, claim 47, after "RHEWNKHGWCNW", insert therein -- (SEQ ID NO:8). --.
Column 46, Line 26, claim 48, please delete "47" and insert therein -- 44 --.

Signed and Sealed this

Seventh Day of August, 2007

JON W. DUDAS
*Director of the United States Patent and Trademark Office*

UNITED STATES PATENT AND TRADEMARK OFFICE
CERTIFICATE OF CORRECTION

PATENT NO. : 7,179,473 B2  Page 1 of 1
APPLICATION NO. : 09/325542
DATED : February 20, 2007
INVENTOR(S) : Meyers It is certified that error appears in the above-identified patent and that said Letters Patent is hereby corrected as shown below:

On the cover page, item

[*] Notice: Subject to any disclaimer, the term of this patent is extended or adjusted under 35 USC 154(b) by 670 days Delete the phrase "by 670" and insert -- by 520 days --

Signed and Sealed this

Eighth Day of April, 2008

JON W. DUDAS
*Director of the United States Patent and Trademark Office*